United States Patent
Dabney

(10) Patent No.: US 11,875,905 B1
(45) Date of Patent: Jan. 16, 2024

(54) SALUBRITY RETENTION SYSTEM USING SELECTIVE DIGITAL COMMUNICATIONS

(71) Applicant: Laura Dabney, Virginia Beach, VA (US)

(72) Inventor: Laura Dabney, Virginia Beach, VA (US)

( * ) Notice: Subject to any disclaimer, the term of this patent is extended or adjusted under 35 U.S.C. 154(b) by 0 days.

(21) Appl. No.: 18/180,587

(22) Filed: Mar. 8, 2023

(51) Int. Cl.
- *G16H 80/00* (2018.01)
- *G16H 15/00* (2018.01)
- *G16H 20/70* (2018.01)

(52) U.S. Cl.
CPC ............. *G16H 80/00* (2018.01); *G16H 15/00* (2018.01); *G16H 20/70* (2018.01)

(58) Field of Classification Search
USPC .......................................................... 705/2
See application file for complete search history.

(56) References Cited

U.S. PATENT DOCUMENTS

| | | |
|---|---|---|
| 7,062,251 B2 | 7/2006 | Birkett et al. |
| 7,248,688 B2 | 7/2007 | Wellons et al. |
| 7,660,413 B2 | 2/2010 | Partovi et al. |
| 8,019,622 B2 | 9/2011 | Kaboff et al. |
| 8,237,551 B2 | 8/2012 | Sweeney et al. |
| 8,699,688 B2 | 4/2014 | Wellons et al. |
| 8,949,137 B2 | 2/2015 | Crapo et al. |

(Continued)

FOREIGN PATENT DOCUMENTS

| | | |
|---|---|---|
| CA | 2616111 C | 6/2014 |
| EP | 2223279 B1 | 5/2020 |

(Continued)

OTHER PUBLICATIONS

Lee, C. (2021). Machine learning frameworks for data-driven personalized . . . clinical impact (Order No. 28715468). Available from ProQuest Dissertations and Theses Professional. (2572589064). Retrieved from https://dialog.proquest.com/professional/docview/2572589064?accou (Year: 2021).*

(Continued)

*Primary Examiner* — Christopher L Gilligan
*Assistant Examiner* — Bennett Stephen Erickson
(74) *Attorney, Agent, or Firm* — ePatentManager; Guerry L. Grune

(57) ABSTRACT

One or more devices that provides an immersive cerebral salubrity retention and selection package (ICSRSP) to potential new patients (PNPs) comprising customized cerebral salubrity care personnel with available personal time periods to improve their cerebral salubrity. An ICSRSP determines whether a PNP qualifies for a cerebral health immersion program (CHIP). The ICSRSP generates a set of interrogatives based on data and data sets (used for a determination) that are not included in initially collected data regarding the PNP. The PNP's acceptance into the ICSRSP is based on an assessment of the PNP data and PNP-provided responses to the interrogatives. If the PNP is selected for the CHIP, an option is provided to the PNP to enroll in the CHIP to become a patient. If additional information is needed to complete an acceptance process for the CHIP, a user interface is provided enabling the PNP to provide data for process completion.

24 Claims, 6 Drawing Sheets

(56) References Cited

U.S. PATENT DOCUMENTS

| | | |
|---|---|---|
| 8,990,834 B2 | 3/2015 | Mathur |
| 9,703,927 B2 | 7/2017 | Chaudhri et al. |
| 9,794,408 B2 | 10/2017 | Turcan et al. |
| 10,037,710 B2 | 7/2018 | Rapparport et al. |
| 10,419,405 B2 | 9/2019 | Westin et al. |
| 10,649,988 B1 | 5/2020 | Gold et al. |
| 11,361,386 B2 | 6/2022 | Phillips |
| 11,380,435 B2 | 7/2022 | Hoffman et al. |
| 2004/0236601 A1 | 11/2004 | Summers et al. |
| 2009/0259493 A1 | 10/2009 | Venon et al. |
| 2011/0295961 A1 | 12/2011 | Wilkes et al. |
| 2013/0179192 A1 | 7/2013 | Rajendran et al. |
| 2014/0257852 A1* | 9/2014 | Walker .................. G06Q 10/10 705/3 |
| 2014/0372147 A1 | 12/2014 | White et al. |
| 2016/0019348 A1 | 1/2016 | Boston et al. |
| 2021/0327582 A1* | 10/2021 | Joshi ..................... G16H 50/20 |
| 2022/0328198 A1* | 10/2022 | Wasan ................... G16H 50/20 |
| 2022/0343065 A1 | 10/2022 | Lord et al. |
| 2022/0344059 A1* | 10/2022 | Clark ..................... G16H 50/30 |
| 2022/0384003 A1* | 12/2022 | Gnanasambandam ...................... G16H 10/60 |

FOREIGN PATENT DOCUMENTS

| | | |
|---|---|---|
| KR | 20-2011-0000014 U | 1/2011 |
| TW | 200933503 A | 8/2009 |
| WO | 2009/039124 A1 | 3/2009 |

OTHER PUBLICATIONS

Sawarkar, S., Shaikh, H., Kshirsagar, V., Machale, P., Shahabade, R. An Android Application for Electronic Health Record System. International Research Journal of Engineering and Technology (IRJET). vol. 6. Issue 3. p. 2569-2570. Mar. 2019.

Mandellos, G.J. et al. Requirements and Solutions for Advanced Telemedicine Applications. Biomedical Engineering. May 2014. https://www.researchgate.net/publication/221906170.

Robertson, Matthew and Ford, Claire (2020) Care of the surgical patient: part 1. British Journal of Nursing, 29 (16). pp. 934-939. ISSN 0966-0461. Northumbria Research Link: http://nrl.northumbria.ac.uk/id/eprint/43428/.

Loper et al.: Enabling flexible integration of healthcare information using the entity-attribute-value storage model. Health Information Science & Systems 2013 1:9.

* cited by examiner

SALUBRITY RETENTION SYSTEM USING SELECTIVE DIGITAL COMMUNICATIONS

DESCRIPTION

This disclosure describes one or more device(s) and system(s) for cerebral salubrity care practitioners and life coaches to facilitate their practice(s) by allowing these practitioners the ability to focus on patients/consumers/clients that are able to participate in an immersive cerebral salubrity care experience. These devices and systems provide automated functionality that quickly distills information about each of the patients/consumers/clients to either be selected or not for maintaining a necessary cerebral salubrity care immersion experience. This immersion program allows for a mutually beneficial and positive patient/practitioner outcome. Practitioners with proper medical credentials can utilize the automated device(s) and system(s) so that they may focus on an immersion program. Often these practitioners are required in order that one or more consumers/patients/clients may not or cannot complete the necessary program to achieve or reestablish their cerebral salubrity goals.

BACKGROUND

Due to a multitude of issues, such as the rising number of cerebral salubrity patients and services, consumers/patients/clients who utilize cerebral salubrity services are increasing, and cerebral salubrity care service personnel must consider customized cerebral salubrity services. While cerebral salubrity service personnel oftentimes provide customized care through various cerebral salubrity modification programs, the burden to apply such customized programs based on patient/consumer needs requires vast amounts of time. Oftentimes, patients/consumers/clients may be unaware that such preparation, personnel, and follow-up is required. Further, cerebral salubrity care processes can be tedious and time-consuming. During this tedious, time consuming cerebral salubrity care process, the staff/administrators may be required to provide an immersive out-patient program which should allow for potential unlimited access to the cerebral salubrity provider, life coach, or relationship coach. The patient/consumer in need of the cerebral salubrity care and/or life coach advising experience is capable of monopolizing most or all of the medical staff personnel time, without empathy, in their time(s) of (at least) perceived immediate need.

Most previous systems have not been designed and focused primarily on the consumers/patients/clients in need of cerebral salubrity care. These systems often direct (warranted) attention to the needs of the cerebral salubrity care provider(s). These cerebral salubrity care practitioners, however, are often overwhelmed with requests but must still remain financially solvent in order to establish and/or continue their customized and much desired and needed immersive cerebral salubrity care practice. Customized immersive cerebral salubrity care practice is increasingly difficult to offer and maintain as it requires intense time and commitment from the practitioner(s) and their staff. To provide the ultimate positive patient outcomes which includes reducing and/or eliminating often chronic cerebral salubrity conditions, the practitioner(s) and their staff must properly screen these patients to determine if their focus and commitment will result in the mutually desired (patient/practitioner) outcomes. This disclosure provides a solution to these issues for the cerebral salubrity care practitioner while also maintaining an equitable outcome for those in need of relief from often chronic cerebral salubrity conditions.

SUMMARY

Aspects of the present disclosure provide an automated selection and ultimately cerebral salubrity immersion program for consumers/patients/clients interested in participating in an immersive cerebral salubrity care protocol and overall treatment process as well as receiving relationship therapy and coaching. An immersive cerebral salubrity retention and selection package (ICSRSP) determines whether a potential new patient (PNP) should be accepted for an immersive program that offers treatment for an ongoing mental, emotional, or relationship need with a service provider. The ICSRSP generates a set of interrogatories based on data (used to make such a determination) that are not included in collected PNP(s) data. The PNP(s) are selected (enrolled) based on an assessment of the PNP data, and PNP provided responses to the interrogatives. If the PNP is selected for participation in the cerebral health immersion program (CHIP), an option is provided to the PNP to enroll in the CHIP. If additional information is needed to complete a selection process for the CHIP, an ICSRSP interface is provided that enables the PNP to provide the data for completing the process.

More specifically the present disclosure describes one or more devices comprising an automated response to one or more individuals that receive an immersive cerebral salubrity retention and selection package (ICSRSP) that is managed by a customized cerebral health immersion program (CHIP) together with available advising session time periods to begin improvement of the individuals' cerebral care, the devices comprising:

at least one processor device; and a memory storage device with instructions that when executed by the at least one processor device is configured to provide a request generator, the request generator configured to receive a request from one or more individuals that become receivers for determination if one or more potential new patients (PNPs) will receive the ICSRSP that includes the one or more receivers receipt of a network of customized cerebral salubrity care personnel;

wherein the one or more receivers complete one or more interrogatives that determine if the one or more receivers are disqualified as a client based on responses that include past and current cerebral salubrity needs and future expectations that the one or more receivers describe with regard to their specific individual cerebral salubrity care issues and wherein program provider rules are applied to consider data acquired from the one or more receivers that are in potential receipt of the ICSRSP such that the devices retrieve PNPs data that includes one or more PNPs personal information selected from a group consisting of; past and current state of cerebral salubrity, human interactions, relationships, and wealth status conditions to analyze cerebral salubrity care service needs, and wherein:

a host acts on behalf of one or more salubrity care service personnel to determine if a PNP can be provided the ICSRSP as determined by one or more cerebral salubrity care service personnel by collection of personal information data via receipt of the personal information data from the PNPs, wherein the personal information data includes retrieval of wealth status data that can also include retrieval from a third-party wealth status data source, and wherein the personal information is data that further includes data generated from and response to a request comprising at least three interrogatives, wherein the interrogatives correlate with personal information data that does not include personal PNP wealth status data;

and wherein the devices transmit the request to a portal configured to generate a potential new patient graphical (PNP) user interface for display to one or more PNPs, wherein the PNP graphical user interface includes the request;

and wherein the one or more salubrity care personnel receive PNP responses to the request via the PNP graphical user interface; and transmits the responses to a filter determinator that is configured to;

receive PNP responses;

assess the PNP responses, personal PNP data, and PNP wealth status data by utilization of the filter determinator to assist with final determination of the responses that includes specific criteria and determines if reception of an ICSRSP is justified via the specific criteria and;

transmits a response to a portal for display to the PNP in the PNP graphical user interface and;

also provides an acceptance determinator, the acceptance determinator configured to receive, via a portal, a request for acceptance into the ICSRSP in order for the PNP to become a bona fide client by identification via the filter determinator if the PNP is allowed based upon program rules that provides acceptance of the PNPs concurrent with all program rules and data provided by the client and the host.

Here, the specific criteria is embedded within the filter determinator and includes at least three interrogatives comprising;

(i) the PNPs immediate cerebral salubrity issue, (ii) timing and length of time required to address the PNPs cerebral salubrity needs, and;

(iii) PNPs ability to engage to succeed by an improvement in cerebral salubrity with customized cerebral salubrity care providers that possess associated advising time periods determined by one or more members of the host and further determines if the PNP is allowed to receive ICSRSP assistance and become a bona fide client.

The specific criteria and the host individually and/or separately can determine if a PNP becomes the bona fide client the bona fide client is informed of a decision by transmission of data that is in a form of a response to the portal for display to the PNP via the PNP user interface, wherein the PNP user interface is displayed on one or more of a group of selected virtual or real devices consisting of; a smart and/or cellular mobile phone, a laptop computer, a desktop computer, a smart watch, a television and a theatre screen.

If the PNP is deemed allowable, the PNP is directed to an auto link that provides R-Rx products to the PNP, wherein the R-Rx products are a collection of treatment options to assist an accepted client with relationship issues that include both low cost and free resources available from at least one of a group consisting of e-books, videos, in-person and on-line advising, seminars, webinars, and hard copy books and manuals.

If the PNP is deemed at least partially allowed into the ICSRSP a potential client is directed to a video that plays in a range of 45 to 90 minutes and/or an in-person session with a trained associate to ascertain if the at least three interrogatives have been completed.

If the PNP becomes a client by passing all assessments, the client is then encouraged to engage with the host and receive an ICSRSP package with an allocation for at least 6 months and to receive an unlimited treatment and access to ICSRSP management personnel with advising times available throughout a 24/7 time period during the unlimited treatment.

The unlimited treatment further comprises provision of salubrity products, access to private locked waiting virtual and/or real waiting areas, and electronic communication options including personal notes taken during salubrity sessions.

In another embodiment the unlimited treatment further comprises automated acceptance with on-line links for additional time period access with the host and a series of electronic communications that include text, video, and voice about salubrity products.

If the clients do not acquire one or more treatment packages that are a portion of the ICSRSP, the clients receive a series of electronic communications and subsequent notifications that continue to be sent until the accepted clients acquire the treatment packages or the accepted clients notify the host to cease and desist from future electronic communications.

If the receivers do not pass all assessments, the receivers receive information that provides the receivers with one or more other hosts and a series of electronic communications that provide R-Rx products.

A determination of the accepted client's information utilizes a request generator configured to send and also receive a request for a determination of one or more PNPs data and continue receipt of records to evaluate ongoing improvement in the accepted clients' cerebral salubrity.

In another embodiment, the ICSRSP is securitized with one or more devices comprising a real or virtual master distributed auto-synchronous array (DASA) database (dB) located within or external to the devices that at least stores and retrieves data and that includes at least two or more partial distributed auto-synchronous array (DASA) dBs wherein the partial DASA dBs function in either an independent manner, a collaborative manner or both, and wherein the master and partial DASA dBs allow for bi-directional transmission of data to and from multiple partial user devices, to and from multiple partial access devices or to and from both partial user and partial access devices, wherein the one or more partial user and access devices store and provide at least partial copies of portions of the master DASA dB and wherein the master DASA dB, the partial DASA dBs or both partial and master DASA dBs are linked and communicate with each other as well as one or more logging and monitoring dBs capable of statistical and numerical calculations utilizing the data, wherein the tools authenticate using a first set of computing operations, validates using a second set of computing operations, and wherein a third set of computing operations controls access for a specified set of users.

Here it also possible for the devices to utilize an artificial intelligence and machine learning infrastructure system comprising:

one or more storage systems comprising, respectively, one or more storage devices included within respective storage arrays controlled by respective one or more storage controllers; and one or more graphical processing units, wherein the graphical processing units are configured to communicate with the one or more storage systems over a communication fabric;

wherein the one or more storage systems, the one or more graphical processing units, and the communication fabric is implemented within a single chassis; and wherein the one or more storage systems are configured to:

receive, at a storage system from the one or more graphical processing units via a storage system application program interface (API) provided by the storage system directly to the one or more graphical processing units and configured to provide specification of one or more data storage operations, one or more data storage operations specifying storage of multiple data objects that respectively include data and metadata describing one or more attributes of the data;

receive, at the storage system from the one or more graphical processing units via the storage system API further configured to provide specification of one or more queries that operate on metadata for the multiple data objects, a query that includes metadata that specifies one or more attributes of data;

generate, based on the storage system searching through the metadata of data objects stored in the storage system, a dataset that includes one or more of the multiple data objects such that the metadata of each data object in the dataset satisfies the one or more attributes of data specified by the metadata included in the query; and transmit, from the storage system to the one or more graphical processing units over the communication fabric, the dataset of the one or more of the multiple data objects.

In addition the present disclosure describes one or more systems that provide an automated response to one or more individuals that are initially receivers and receive an immersive cerebral salubrity management program comprising customized cerebral salubrity care with advising time periods to begin improvement of the individuals' cerebral salubrity, the systems comprising:

to one or more individuals that receive an immersive cerebral salubrity retention and selection package (ICSRSP) that manages customized cerebral care together with available advising session time periods to begin improvement of the individuals' cerebral care, the devices comprising:

at least one processor device; and a memory storage device with instructions that when executed by the at least one processor device is configured to provide a request generator, the request generator configured to receive a request from one or more individuals that become receivers for determination if one or more potential new patients (PNPs) will receive the ICSRSP that includes one or more receivers receipt of a network of customized cerebral salubrity care personnel;

wherein the one or more receivers complete one or more interrogatives that determine if the one or more receivers are disqualified as a client based on responses that include past and current cerebral salubrity needs and future expectations that the one or more receivers describe with regard to their specific individual cerebral salubrity care issues and wherein program provider rules are applied to consider data acquired from the one or more receivers that are in potential receipt of the ICSRSP such that the devices retrieve PNPs data that includes one or more PNPs personal information selected from a group consisting of; past and current state of cerebral salubrity, human interactions, relationships, and wealth status conditions to analyze cerebral salubrity care service needs, and wherein:

a host acts on behalf of one or more salubrity care service personnel to determine if a PNP can be provided the ICSRSP as determined by one or more cerebral salubrity care service personnel by collection of personal information data via receipt of the personal information data from the PNPs, Wherein the personal information data includes retrieval of wealth status data that can also include retrieval from a third-party wealth status data source, and wherein the personal information is data that further includes data generated from and response to a request comprising at least three interrogatives, wherein the interrogatives correlate with personal information data that does not include personal PNP wealth status data;

and wherein the devices transmit the request to a portal configured to generate a potential new patient graphical (PNP) user interface for display to one or more PNPs, wherein the PNP graphical user interface includes the request;

and wherein the one or more salubrity care personnel receive PNP responses to the request via the PNP graphical user interface; and transmits the responses to a filter determinator that is configured to;

receive PNP responses;

assess the PNP responses, personal PNP data, and PNP wealth status data by utilization of the filter determinator to assist with final determination of the responses that includes specific criteria and determines if reception of an ICSRSP is justified via the specific criteria and;

transmits a response to a portal for display to the PNP in the PNP graphical user interface and;

also provides an acceptance determinator, the acceptance determinator configured to receive, via a portal, a request for acceptance into the ICSRSP in order for the PNP to become a bona fide client by identification via the filter determinator if the PNP is allowed based upon program rules that provides acceptance of the PNPs concurrent with all program rules and data provided by the client and the host.

In this system, the specific criteria is embedded within the filter determinator and includes at least three interrogatives comprising;

(i) the PNPs immediate cerebral salubrity issue, (ii) time period and timing required to address the PNPs cerebral salubrity needs, and (iii) PNPs ability to engage effectively with customized cerebral salubrity care personnel with associated advising time periods that is determined by one or more members of the host and further determines if the PNP can receive assistance and become a bona fide client.

Again, the specific criteria and the host that individually and/or separately determines if a PNP is accepted to become a client is informed of a decision by transmission of data that is in a form of a response to the portal for display to the PNP via the PNP graphical user interface that displays the response on one or more of a group of selected devices consisting of; a smart and/or cellular mobile phone, a laptop computer, a desktop computer, a smart watch, a television and a theatre screen.

For this system if the PNP is deemed disqualified the PNP is directed to an auto link that provides R-Rx products to the PNP, wherein the R-Rx products are a collection of treatment options to assist an accepted client with relationship issues that include both low cost and free resources available from at least one of a group consisting of e-books, videos, in-person and on-line advising, seminars, webinars, and hard copy books and manuals.

In addition, the system determines if the PNP is deemed at least conditionally accepted the client is directed to a video that plays in a range of 45 to 90 minutes and/or to an in-person session with a trained associate of the host to clarify the at least three interrogatives have been completed.

Another embodiment of the system determines if the PNP becomes a client by passing all assessments , the client is then encouraged to engage with the host and receive an immersive cerebral salubrity management system that manages an ICSRSP with an allocation for at least 6 months and to receive an unlimited treatment and access to a host that provides advising time throughout a 24/7 hour time period during the unlimited treatment.

As with the devices, the unlimited treatment further comprises salubrity products, access to private locked waiting virtual and/or real waiting areas, and electronic communication options including e-mailing of personal notes taken during salubrity sessions.

A further embodiment includes the unlimited treatment further comprising an automated acceptance with on-line links for additional time periods and electronic communication series for additional salubrity products.

Again, if the accepted clients do not acquire the treatment package, they receive a series of electronic communications and subsequent notifications that continue to be sent until they acquire the treatment packages or the accepted clients notify the host to cease and desist from future electronic communications.

If the receivers do not pass all assessments, they receive information that provides the receivers with one or more other hosts and a series of electronic communications that provide R-Rx products.

For this and similar systems a determination of the client's information utilizes a request generator configured to send and also receive a request for a determination of one or more PNPs data and continue receipt of records to evaluate ongoing improvement in the clients' cerebral salubrity.

In another embodiment the system is securitized with one or more devices comprising a real or virtual master distributed auto-synchronous array (DASA) dB located within or external to the devices that at least stores and retrieves data and that includes at least two or more partial distributed auto-synchronous array (DASA) dBs wherein the partial DASA dBs function in either an independent manner, a collaborative manner or both, and wherein the master and partial DASA dBs allow for bi-directional transmission of data to and from multiple partial user devices, to and from multiple partial access devices or to and from both partial user and partial access devices, wherein the one or more partial user and access devices store and provide at least partial copies of portions of the master DASA dB and wherein the master DASA dB, the partial DASA dBs or both partial and master DASA dBs are linked and communicate with each other as well as one or more logging and monitoring dBs capable of statistical and numerical calculations utilizing the data, wherein the tools authenticate using a first set of computing operations, validates using a second set of computing operations, and wherein a third set of computing operations controls access for a specified set of users.

Here the system utilizes an artificial intelligence and machine learning infrastructure system comprising:

one or more storage systems comprising, respectively, one or more storage devices included within respective storage arrays controlled by a respective one or more storage controllers; and one or more graphical processing units, wherein the graphical processing units are configured to communicate with the one or more storage systems over a communication fabric;

wherein the one or more storage systems, the one or more graphical processing units, and the communication fabric are implemented within a single chassis; and wherein the one or more storage systems are configured to:

receive, at a storage system from the one or more graphical processing units via a storage system application program interface (API) provided by the storage system directly to the one or more graphical processing units and configured to provide specification of one or more data storage operations, one or more data storage operations specifying storage of multiple data objects that respectively include data and metadata describing one or more attributes of the data;

receive, at the storage system from the one or more graphical processing units via the storage system API further configured to provide specification of one or more queries that operate on metadata for the multiple data objects, a query that includes metadata that specifies one or more attributes of data;

generate, based on the storage system searching through the metadata of data objects stored in the storage system, a dataset that includes one or more of the multiple data objects such that the metadata of each data object in the dataset satisfies the one or more attributes of data specified by the metadata included in the query; and transmit, from the storage system to the one or more graphical processing units over the communication fabric, the dataset of the one or more of the multiple data objects.

Examples of implementing this system includes a computer process, a computing system, or as an article of manufacture such as a device, computer program product, or computer readable media, According to an aspect of the present disclosure, the computer program/product is a computer storage media readable by a computer system and encoding a computer program of instructions for executing a computer process. This can be implemented using one of many hardware devices such as smart phones, laptop and desktop computers, and includes eye ware and other wearable devices.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims,

BRIEF DESCRIPTION OF THE DRAWINGS

Further features, aspects, and advantages of the invention represented by the examples described in the present disclosure will become better understood by reference to the following detailed description, appended claims, and accompanying Figures, wherein elements are not to scale so as to more clearly show the details, wherein like reference numbers indicate like elements throughout the several views, and wherein:

DETAILED DESCRIPTION

Figure 1:
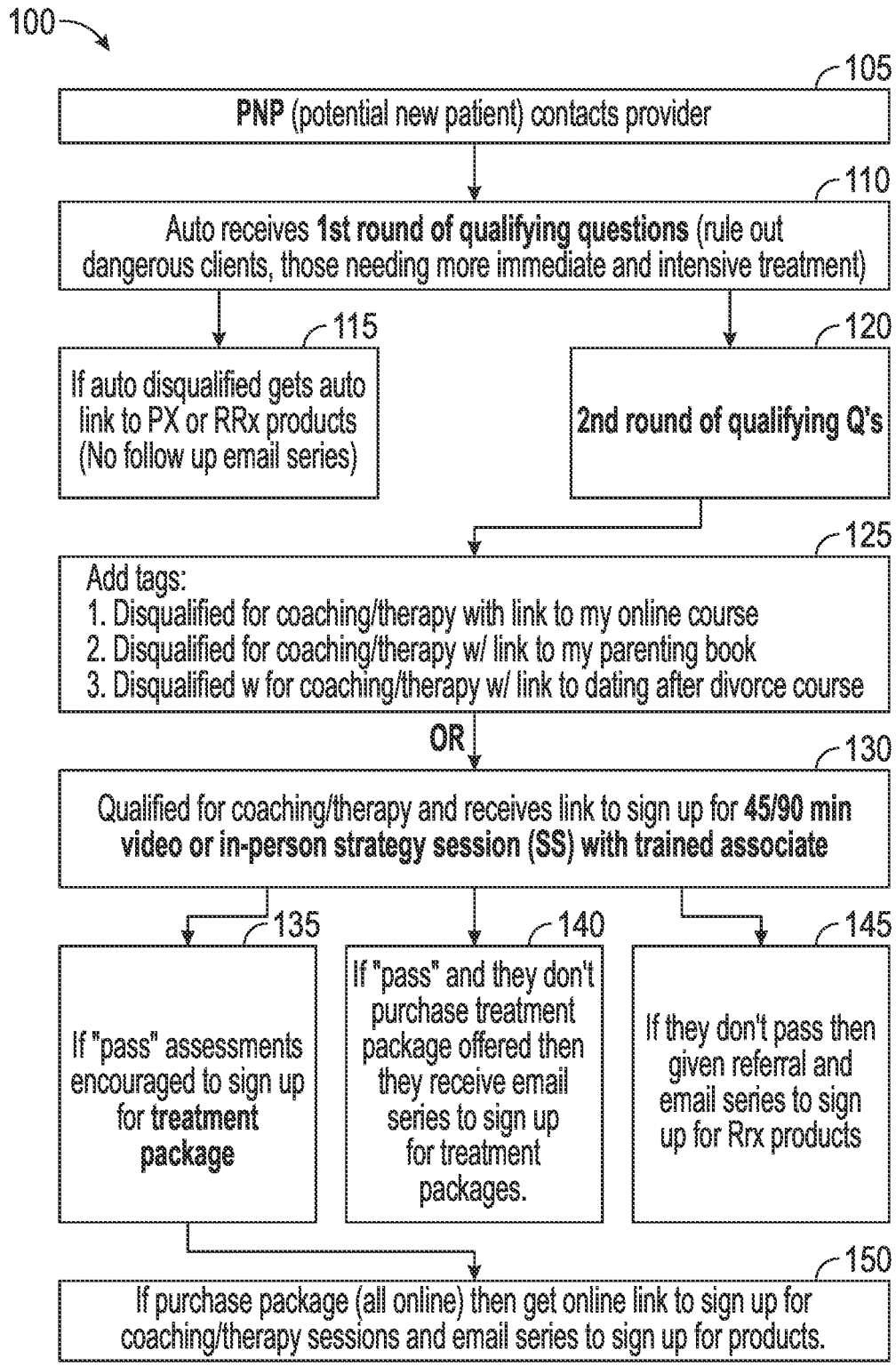
FIG. 1 is a schematic illustration of a logic flow diagram that indicates how a practitioner or host initiates an automated process to determine if a PNP/consumer/patient is able to participate in an immersive cerebral salubrity retention and selection package (ICSRSP) using selective digital communications.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not to be taken in a limiting sense.

As described herein, an automated selection and retention process for an immersive customized cerebral salubrity management system is presented. An immersive cerebral salubrity retention and selection package (ICSRSP) determines whether a potential new patient (PNP) should be accepted for an immersive program that offers treatment for an ongoing mental, emotional, or relationship need with a service provider. Even more specifically, an emotional and relational salubrity retention and selection system (or simply "system") enables and facilitates a counseling/therapy campaign via the system on behalf of one or more individuals who wish to receive psychiatric help and/or life coaching for themselves and/or direct relationships from the practitioner/host. Herein a host is defined as an entity that acts on behalf of one or more persons including administration/staff and/or one or more practitioners that are able to initiate a customized cerebral salubrity care management system. The devices and associated processes utilized to initiate such a system identifies a receipt of a message from one or more individual(s) that are potential consumers/patients/clients that may be capable of being selected for this customized cerebral salubrity care management system. The host invites other participants to join group sessions. The host controls the system and makes the final approval to deliver one or more messages to the one or more PNPs. The potential new patient is the person to whom the message is intended for, and whom the host has identified as the target of the system. A participant is a person invited by the host to join the system. The participant can be, for example, a friend, a relative, a co-worker, or other individual needed for the well-being of the potential new patient who may or may not become a consumer/patient/client. A professional counselor or psychiatrist may get involved in a system to assist the host and participants in the creation of the message intended for the PNP.

Herein is provided devices that utilize systems and methods via computer readable storage devices including computer readable instructions, which when executed by a processing unit, provide automated Cerebral Health Immersion Program (CHIP) selection options. FIG. 1 is a logical flow diagram illustrating a customized emotional and relational salubrity systems and methods for psychiatric and relationship assistance, such as advising and/or coaching, to create an individualized support campaign that includes a (normally automated) messaging system for the one or more individual consumers/patients/clients in order to motivate them to take the first step towards psychiatric treatment(s) and/or relationship help.

This system refers generally to the process of initiating a specific emotional and relationship based artificial intelligence (AI) assisted cerebral salubrity care immersion engagement of the initial receivers who are the potential consumers/patients/clients as determined by the host. The host determines if the potential consumer/patient/client can adequately succeed in an immersive cerebral salubrity care management system. The determination is based on not only if it is possible but also includes whether or not there is a high probability of success and outcome for the eventual patient/practitioner and potential client when entering such a long-term engagement. A system starts with the potential new patient (PNP) providing answers to a set of interrogatories within an immersive cerebral salubrity retention and selection package (ICSRSP) [100].

A PNP contacts the service provider [105]. The initial contact can be in-person or via a device such as a telephone or computer, to place a call, text, or email. Information to initiate the contact with the service provider can be obtained from the providers website, advertisements, or social media. Once contact with the provider is established and contact information for the PNP is obtained, the ICSRSP automatically provides a first round of qualifying questions (1QQ) to the PNP [110], The 1QQ are designed to rule out dangerous clients and those needing more immediate and intensive treatment.

Responses to the 1QQ provide a determination of "Safe" or "1QQ Qualified" and "Unsafe" or "1QQ Disqualified". If auto-disqualification during 1QQ occurs [115], the PNP is provided with links to the providers self-help products and no follow-up email series or campaign is provided. If the PNP is deemed "Safe" or "1QQ Qualified", a second round of qualifying questions (2QQ) is provided [120]. The 2QQ are designed to quickly determine the ability of the PNP to engage in coaching/therapy or a CHIP.

The 1QQ link to the PNP to allow for either scheduling a free 15-minute phone consultation with a trained member of the provider's staff or filling out an additional questionnaire.

Responses to the 2QQ provide a determination of "Safe" or "2QQ Qualified" and "Unsafe" or "2QQ Disqualified". If auto-disqualification during 2QQ occurs [125], the PNP is tagged with one of three tags and is provided with links to the providers online course(s), parenting book(s), or dating after divorce course(s) and no follow-up email series or campaign is provided. If the PNP is deemed "Safe" or "2QQ Qualified", a link for a 45- or 90-minute in-person or virtual strategy session (SS) with a trained associate is provided. During the SS, an intake assessment is conducted as a third round of qualifying questions (3QQ [130]. The 3QQ have been created for a deeper insight into a) the PNPs problem, b) "safety" level of the PNP (e.g. does not need hospitalization, is not med-seeking, has empathy and therefore will not mistreat the practitioner or become a burden on the practice, etc.) and c) the PNPs ability to engage effectively with the provider by testing the insight, abstraction, ego functioning and object relations (ability to engage with others) of the PNP.

Responses to the 3QQ provide a determination of "Safe" or "3QQ Qualified" and "Unsafe" or "3QQ Disqualified". A PNP that has "passed" all assessments with a determination of "Safe" or "3QQ Qualified" is encouraged to sign up for a treatment package [135]. A treatment package consists of unlimited (24/7) treatment access to the providers (thus the need for PNP screening), product discounts, access to a private locked waiting area, video and email therapy, and emailed therapy notes. If the PNP purchases a program package [150], they receive an online link to sign-up [155] for program sessions along with a link to sign up for products and become a patient/client [160].

A PNP that has "passed" all assessments with a determination of "Safe" or "3QQ Qualified" and has received information to sign up for a treatment package, but has not purchased a program package [165], receives an email series or campaign to encourage the PNP to sign-up for a treatment package [140]. A PNP that receives a determination of "3QQ Disqualified" is given a referral to another provider or program for which the PNP may be qualified [145].

Figure 2A:
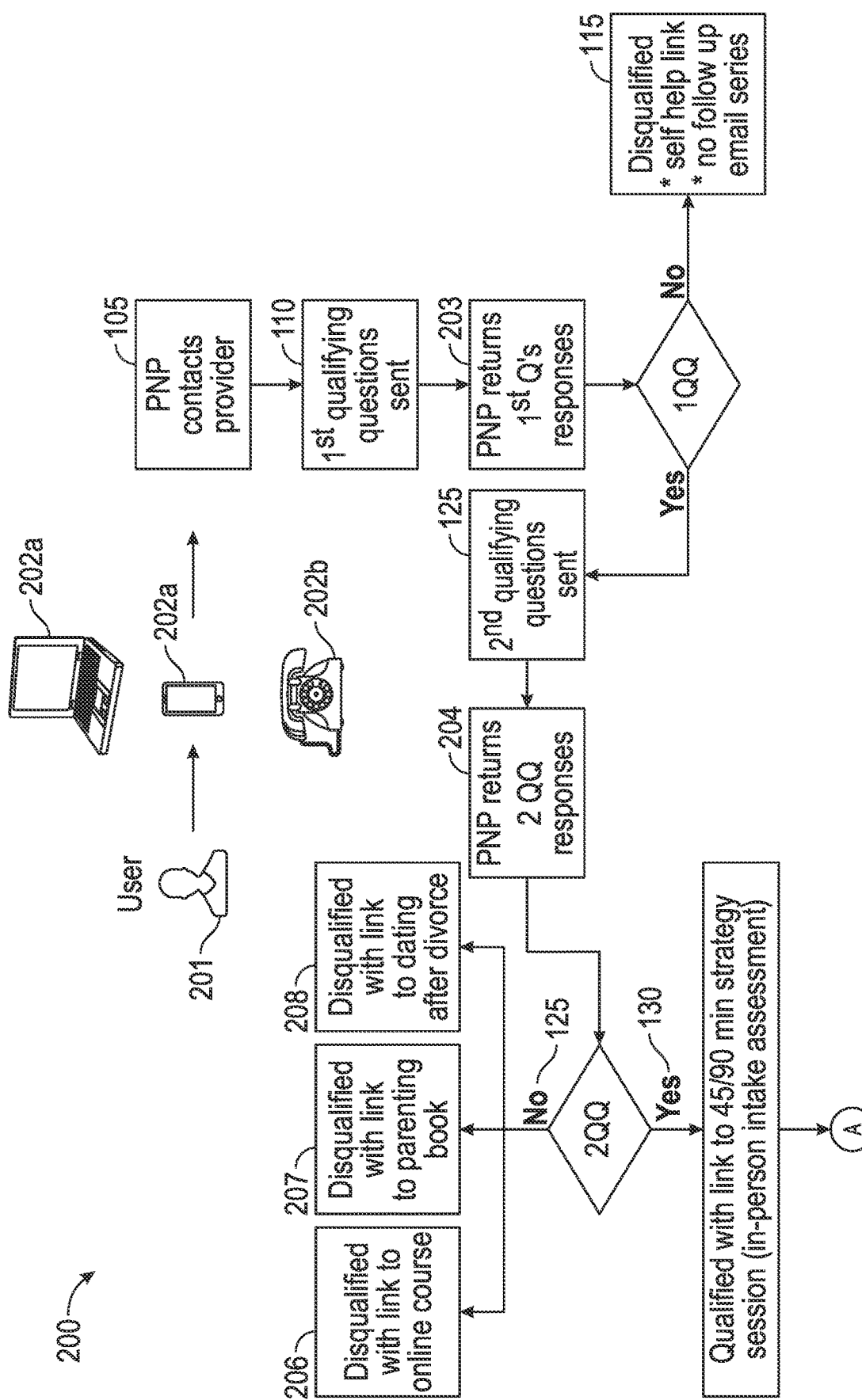
FIGS. 2A 2B are a flowchart depicting the unique devices and processes required to achieve an immersive cerebral salubrity retention and selection package (ICSRSP) using selective digital communications.
Figure 2B:
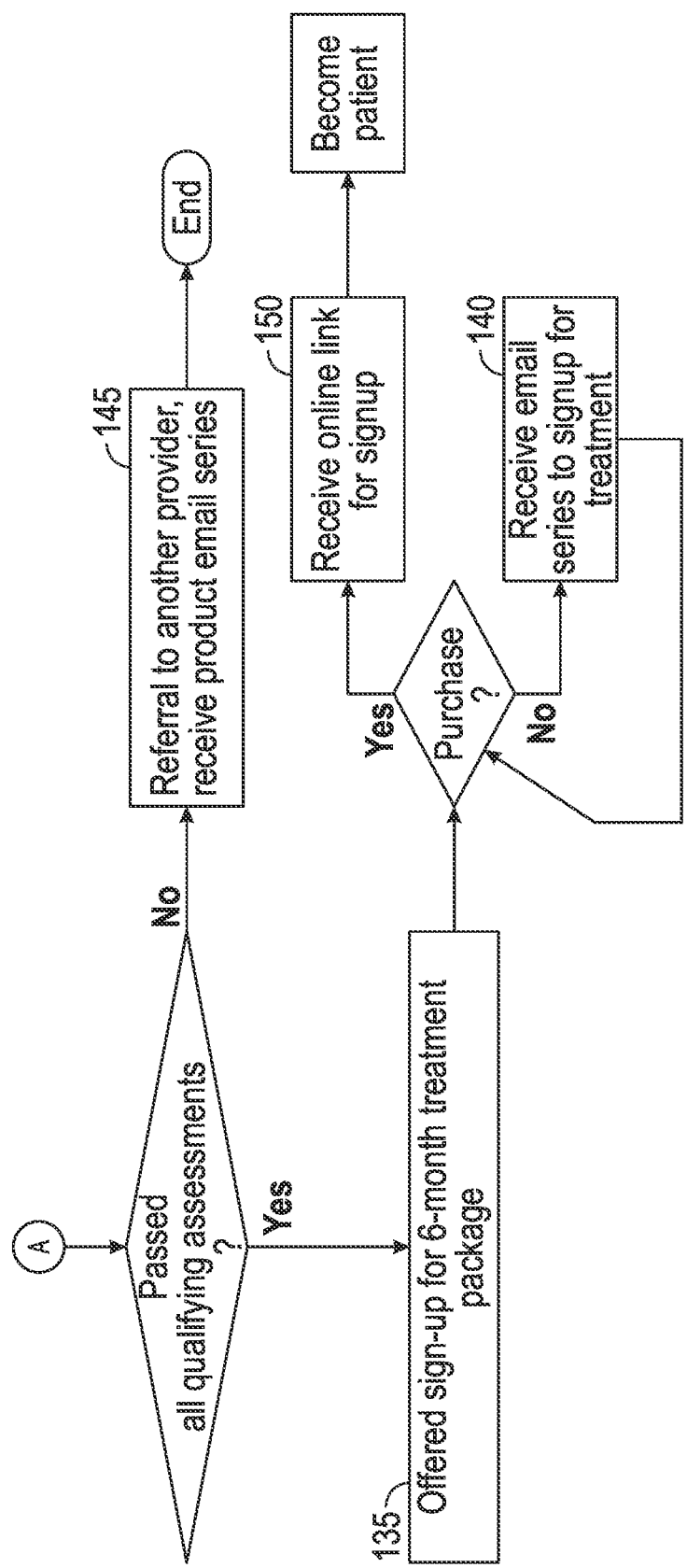

FIGS. 2A and 2B provide a flowchart further depicting the unique devices and processes required to achieve an immersive cerebral salubrity retention and selection package (ICSRSP) using selective digital communications [200]. A PNP, or user [201] contacts a practitioner [105] via a communication device [202], where a user computing device [202a] or a general communication device [202b] can be utilized. After contact, the user [201] receives the 1QQ [110] and provides a 1QQ response [203]. If 1QQ is disqualified as described in FIG. 1, the PNP [201] receives a link to self-help products and no further engagement is received from the ICSRSS [100]. If 1QQ is qualified, the PNP [201]0 receives the 2QQ [120] to which a 2QQ response [204] is provided. If the PNP [201] is 2QQ disqualified [125], one of three tags are used to segment the PNP [201] into 2QQ Disqualified (online course) [206], 2QQ Disqualified (parenting book) [207] and 2QQ Disqualified (Dating After Divorce) [208]. Based on the tag given the PNP [201], a resulting online link is sent to direct the PNP tea the relevant products alternative to the CHIP. The tags and segments can be modified to suit the cerebral salubrity program to which it is being applied.

Figure 3A:
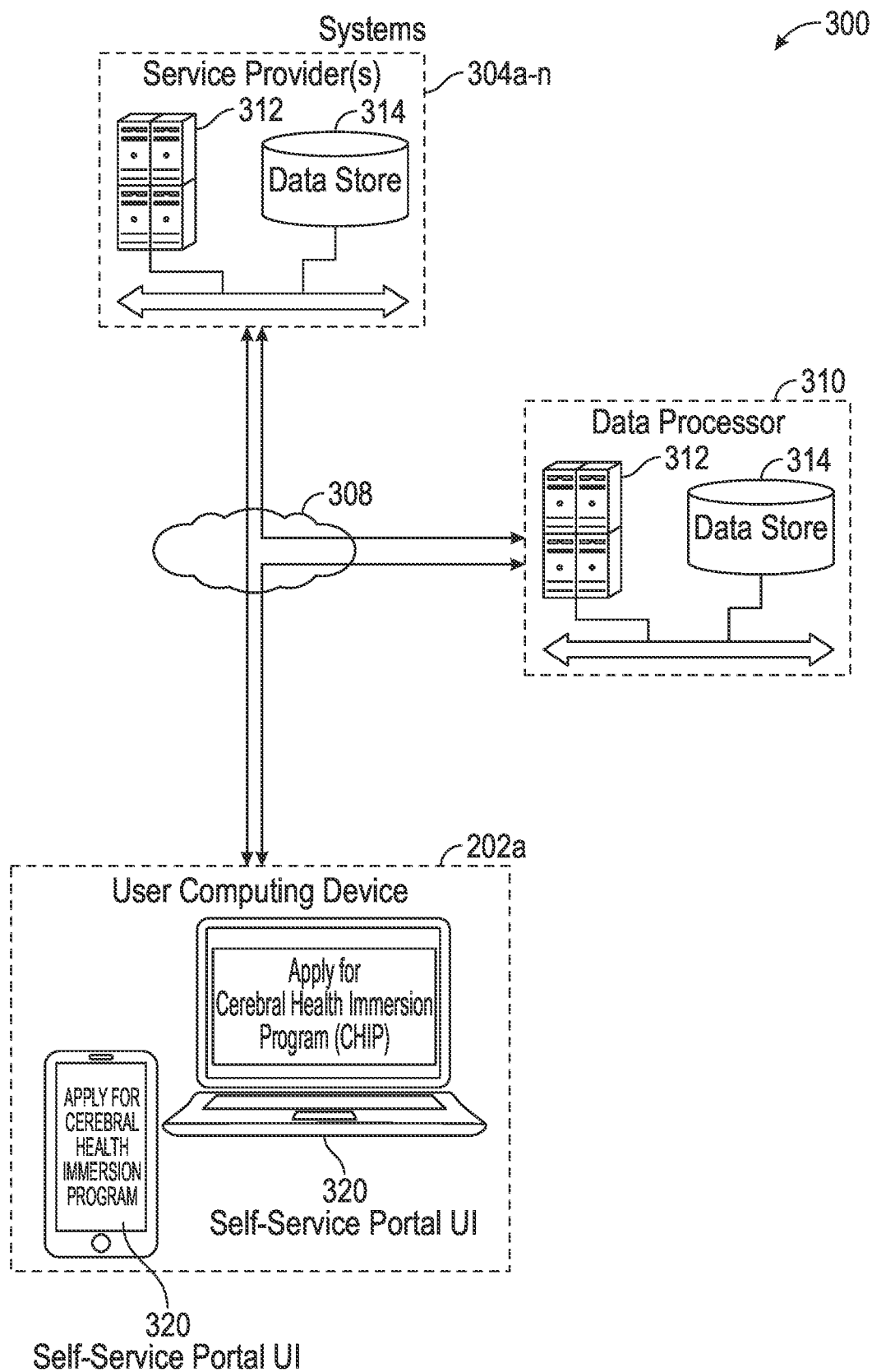
FIG. 3A is a block diagram illustrating an example operating environment in which an immersive cerebral salubrity retention and selection package (ICSRSP) using selective digital communications may be implemented.

FIG. 3A is a block diagram illustrating an example ICSRSP operating environment [300] in which automated assistance program qualification and enrollment, can be performed. Systems within the example ICSRSP operating environment [300] exchange data and perform analytics to determine whether a user qualifies for one or more cerebral health immersion programs (CHIP). A user's qualification for CHIP is determined based on a profile of the user and user-provided answers to a reduced set of qualification questions (QQ) that are customized by the provider based on the aspects of the CHIP. Aspects of the present disclosure further provide instant (e.g., real-time or near real-time) approval and automatic offers of enrollment for users meeting qualifications for a CHIP program. Aspects improve data security and reduce the consumption of computing resources by eliminating transmissions of sensitive data prior to determining a user's qualification based on the user's profile and user responses to the qualification questions (QQ) If a CHIP policy requires supporting documentation, aspects further enable the user to upload the documentation and to provide a signature from a user computing device. Enabling the various systems and computing devices to exchange data provides access to data related to a user that might not otherwise be available. This data exchange further enables the user to discover and access cerebral salubrity programs of which the user may otherwise not be aware, which can minimize or at least lower the probability of the user's reneging on his/her obligations as opposed to a system that requires users to search for and manually apply for various cerebral salubrity programs.

As used herein, the term "cerebral health immersion program" (CHIP) refers to a program that provides immersive assistance to users who have the ability to participate in all or a significant part of their selected CHIP. Such programs can be offered by service providers or by other organizations, such as private companies, charitable organizations, government agencies, and the like, where a qualified service provider is available. Although examples are given herein primarily involving salubrity care providers and patients, it will be recognized that the present disclosure is applicable to several salubrity care fields where providers are faced with the difficulty of qualifying a PNP for provided services. Improvements to the efficiency and security of an ICSRSP not only improve the existing systems themselves but reduce the risks to providers in providing immersive services and improve patient access to cerebral salubrity care.

With reference to FIG. 3A, the example ICSRSP operating environment [300] includes a user computing device [202a], one or more service provider networks [304 a-n] (generally, 304), and a data processor system [310]., Each of the systems [304 and 310] include one or more computing devices [312], include one or more data storage devices [314], and are in communication with a network [308] or a combination of networks for exchanging data and coordinating operations to determine a user's qualification fur a CHIP and to potentially allow for automatic enrollment of users who are determined to qualify. The one or more computing devices [312,202a] are illustrative of a wide variety of computing devices, the hardware of which is discussed in greater detail herein.

The user computing device [202a] can be one of various types of computing devices. Non-limiting examples of user computing devices [202a] include mobile devices, laptop computers, desktop computers, wearable computing devices, and other computing devices suitable to access a self-service portal system, which provides a user interface [320] through which a user can view ongoing transactions, view and provide answers to a set of qualification questions for determining the user's eligibility for a CHIP, receive a CHIP qualification/eligibility response, and, if required, upload and transmit supporting documentation and provide a digital signature to the data processor system [310]. For example, the user computing device [202a] is configured to communicate with the data processor system [310] via the network [308]. The user can be the PNP or consumer receiving services from a service provider, a parent or guardian of the PNP/consumer, or any other person or entity responsible for the PNP/consumer's obligations regarding services rendered. The terms "user", "client", "patient", "PNP", and "consumer" may be used interchangeably herein, The network [308] can be any type of public or private data network for communicating data between computer systems at different entities and at different geographic locations. The Internet is an example of one possible network [308].

The service provider system [304] is configured to generate and store ongoing transaction records relating to consumers. Each ongoing transaction record relates to an encounter with a user and includes information related to a service or services sought by the user or provided to that user. For example, an ongoing transaction record includes any contact between the user and provider, service history including records for different CHIPs, obligation information for an encounter (e.g., a bill, follow-up visits, upcoming additional services) and payment history. Because each service provider generates an ongoing transaction record for a user encounter, there may be multiple ongoing transaction records for each user visit to a provider. For example, a user may participate in a CHIP, need to be treated in a hospital which may result in ongoing transaction records from the hospital, the treating physician, and the lab.

Guidelines and criteria for qualification for a CHIP may be defined by service provider policies and CHIP rules. For example, the service provider system(s) [304] is/are configured to generate and store provider policies that define the service provider's CHIP guidelines. For example, a service provider policy may define types of services that are eligible for CHIP, participating providers (e.g., physicians), qualifiers associated with a user's cerebral salubrity situation, or demographic information, and other service provider-specific guidelines. The service provider system(s) [304] is/are further configured to generate and store CHIP rules for each available CHIP that define each CHIP's criteria for qualification. Non-limiting examples of CHIP rules may define qualifiers associated with medical diagnoses, required services, age, employment status, enrollment in other programs housing status (e.g., homelessness, low-income/subsidized housing residency), etc.

The data processor system [310] is in communication with the service provider system(s) [304], the user's computing device [202a]. The exchange of data and interaction between these systems of the example ICSRSP operating environment [300] is explained in more detail herein.

Figure 3B:
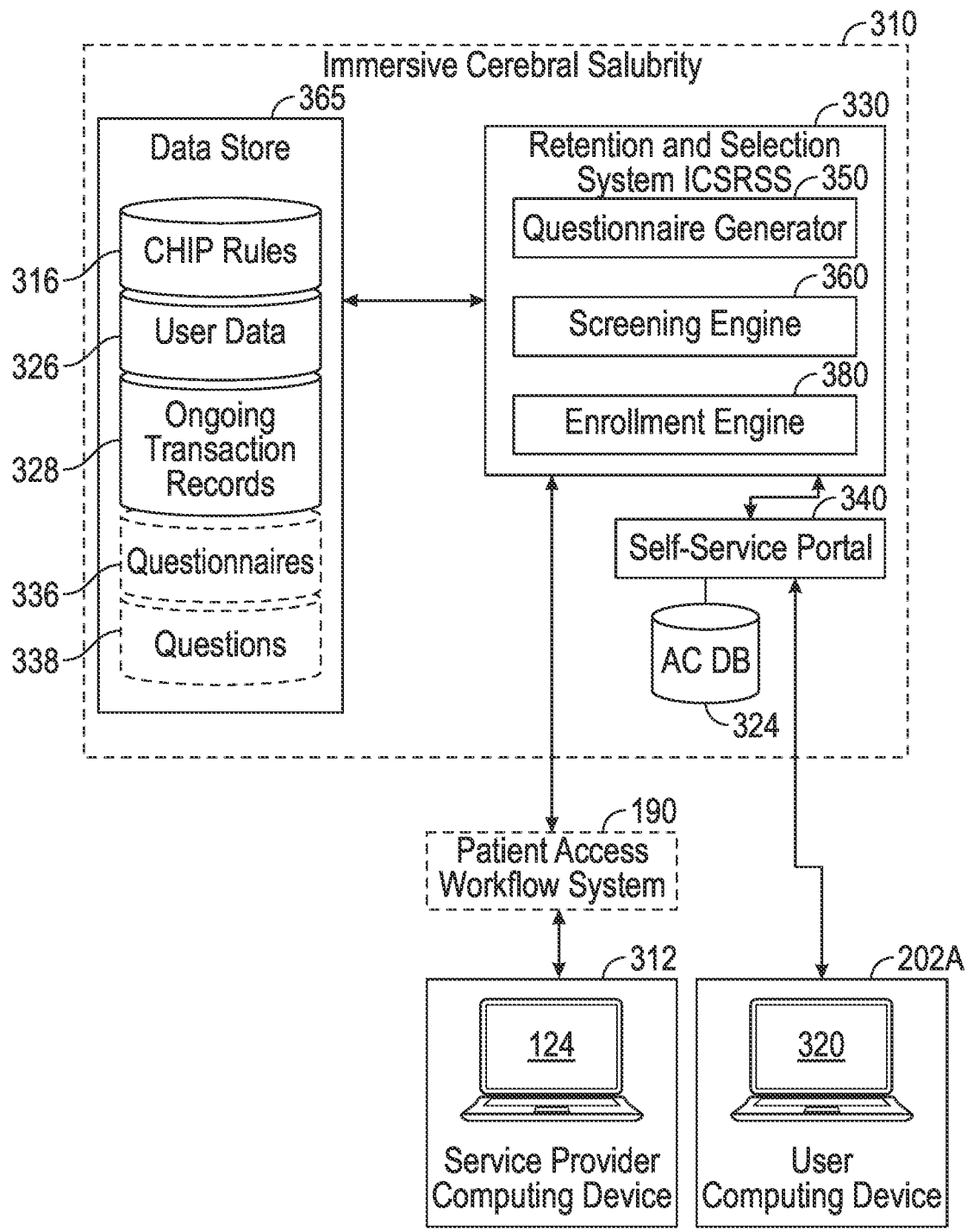
FIG. 3B is a block diagram illustrating an example embodiment of devices used for an immersive cerebral salubrity retention and selection package (ICSRSP) using selective digital communications.

FIG. 3B is a block diagram illustrating an example embodiment of an immersive cerebral salubrity retention and selection system (ICSRSS) [330] that is executed by the data processor system [310]. In this example, the data processor system [310] includes an ICSRSS 330, a self-service portal system [340], and a data store [365]. According to an aspect, the ICSRSS [330] includes a questionnaire generator [350], a screening engine [360], and an enrollment engine [370]. Instructions for the ICSRSS [330] can be executed by a single computing device [312]. Alternatively, instructions for the ICSRSS [330] can be distributed across two or more computing devices that are in communication with each other and form a part of the data processor system [310].

The data store [365] can include memory that forms a part of a computing device or devices executing the ICSRSS [330]. Alternatively, the data store [365] can include separate or secondary storage hardware in communication with the computing device executing the ICSRSS [330]. In various examples, the data store [365] can be a cloud-based storage system that is separate and remote from the data processor system [310] and is also in communication with the data processing system [310] through the network [308]. As will be described in more detail below, the data store [365] stores user data [336] about the user, ongoing transaction records [328], CHIP rules [316] and associated service provider policies, and in some implementations, pre-generated questionnaires [336] for the user and pre-generated questions [338] for inclusion in a questionnaire. In some aspects, the data store [365] stores one or more forms, such as application or enrollment forms, that can be automatically filled with collected and received data and that can be exposed to the user via a self-service portal [340].

The self-service portal [340] is illustrative of a secure web-based application platform that can be accessed by a user agent (e.g., a web browser or a stand-alone application) executing on the user computing device [202a]. According to an aspect, the self-service portal [340] provides authenticated users with access to information related to the user (e.g., the user or a consumer associated with the user). For example, the user can use the self-service portal [340] for one or a combination of the following activities: to see ongoing transaction information associated with one or more service provider account(s), to make online payments or set up payment plans, to schedule appointments, and, according to an aspect of the present disclosure, to qualify for and enroll in a CHIP. In various implementations, the types of information available to users via the self-service portal [340] may be defined by the service provider(s).

In example aspects, the self-service portal [340] is configured to generate a self-service portal user interface (UI) [320] for display on the user computing device [202a] via the user agent. According to an aspect, the self-service portal [340] includes one or more application programming interfaces (APIs), which connect the self-service portal [340] to the ICSRSS [330] so that the self-service portal is able request a CHIP qualification questionnaire from the ICSRSS and to transmit data input by the user via the user computing device [202a] to the ICSRSS for determining whether the user qualifies for a CHIP and to communicate that determination to the user.

In various examples, the sell-service portal [340] includes or is in communication with an access control engine that is configured to authenticate the user using a suitable authentication technology. For example, to access secure user-related content, the self-service portal [340] may require the user to input identifying information to prove that the user is who he/she says that he/she is and to determine what information the user is authorized to access. The access control engine may be configured to verify the identifying information provided by the user against identifying information stored in an access control database [324] that can be a DASA database for verifying the users identify. When the user's identify is successfully authenticated, the access control engine may be further configured to request the user's access privileges against an authorization policy or set of permissions stored in the access control database [324] for determining what information the user is authorized to access. The access control engine may be a single system that is configured to perform authentication and authorization processes; or, the access control engine may include separate authentication and authorization engines, wherein the authentication is configured to perform authentication processes and the authorization engine is configured to perform authorization processes. Likewise, the access control database [324] may be a single database or separate databases.

According to an aspect, the self-service portal [340] is configured to invoke a questionnaire API to request a questionnaire comprising a set of qualification questions from the questionnaire generator to transmit to the user computing device [202a]. Here the API is as typically defined as a set of specifications, such as Hypertext Transfer Protocol (HTTP) request messages, along with a definition of the structure of response messages, usually in an Extensible Markup Language (XML) or JavaScript Object Notation (JSON) format. In example aspects, the self-service portal [340] is configured to request the set of qualification questions from the questionnaire generator [350] responsive to receiving a request for or a selection of CHIP options. For example, the request for or a selection of CHIP options may be user-initiated request/selection initiated via a user input or user selection via the self-service portal UI [320].

The questionnaire generator [350] is illustrative of one Of more software applications, modules, or computing devices operative or configured to generate a questionnaire for acquiring information needed to make a CHIP qualification determination. In example aspects, the questionnaire includes the set of qualification questions that are customized to the user based at least in part on a user profile and the service provider associated with the user. In some example aspects, the questionnaire generator [350] generates the questionnaire dynamically responsive to receiving a request for a set of qualification questions from the self-service portal [340]. In other example aspects, the questionnaire generator [350] proactively generates the questionnaire responsive to receiving an ongoing transaction record [328] associated with a service provided to a user, and stores the questionnaire in the data store [365]. Accordingly, when a request is received for the questionnaire, the questionnaire generator [350] is configured to retrieve the pre-generated questionnaire [336] from the data store [365].

According to an aspect of this disclosure, as part of generating the questionnaire, the questionnaire generator [350] is configured to determine data needed to make a determination as to whether the user qualifies for one or more CHIPs. This data is herein referred to as qualification data. As part of determining what qualification data is needed for determining the user's qualification for assistance with one or more ongoing transaction records [328], the questionnaire generator [350] is configured to access the data store [365] to retrieve CHIP rules [316] associated with one or more service provider policies for generating the questionnaire based on qualification criteria for the CHIPs. In some examples, the questionnaire generator [350] may receive user identifier information and optionally service provider identifier information from the self-service portal [340]. This information may be determined by the self-service portal [340] as part of the log-in process. According to an aspect, the questionnaire generator [350] is configured to access the data store [365] to retrieve ongoing transactions records [328] associated with the user. As described above, ongoing transaction records [328] are provided by the one or more service provider systems [304], and each ongoing transaction record includes information related to a service or services provided to that user by the service provider. Based on which service providers the user has ongoing transaction records [328] with, the questionnaire generator [350] is configured to retrieve those service provider policies from the CHIP rules [316]. For example, a single salubrity care service encounter may include multiple services provided to the user by multiple service providers during a CHIP, such as a hospital, a physician, a lab, a radiology service, etc.; and an ongoing transaction record may be associated with each of these services.

As part of determining the qualification data for a qualification determination, the questionnaire generator [350] is further configured to access the data store [365] to retrieve CHIP rules [316] associated with one or more assistance programs for generating the questionnaire based on qualification criteria for the assistance programs. In some aspects, the CHIP rules [316] are generated by and received from the one or more service provider systems [104] and/or one or more assistance program systems [132]. In other example aspects, the CHIP rules [316] are generated by ICSRSS [330] based on assistant program eligibility criteria provided by the service provider system(s) 104 and/or the assistance program system(s). For example, ICSRSS [330] is utilized to pre-qualify/qualify the user for and enroll the user in an CHIP from CHIP providers who are part of or who have contracted with the salubrity care service provider (or a third-party provider of a patient access workflow system [390] utilized by the salubrity care service provider system [304] via a service provider computing device [322]. The CHIP rules [316] may be stored as rules that define specific data to evaluate and an action to be taken when the rule is evaluated as true. Based on the specific data to be evaluated according to specific CHIP rules [316], the questionnaire generator [350] determines needed qualification data for a qualification determination.

When qualification data needed to make a qualification determination for one or more available CHIPs are determined (e.g., based on available CHIP rules [316]) the questionnaire generator [350] is further configured to obtain one or more qualification data items from one or more data sources. According to an aspect, the questionnaire generator [350] is configured to access the data store [365] to retrieve qualification data stored as user data [326] associated with the user.

In example aspects, user data [326] can include data collected by and received from the service provider system [304], and can include data collected as part of a registration process for the user and data produced as part of providing services to the user. For example, user data [326] can include demographic data about the user, such as but not limited to: first name, middle name/initial, last name, address, telephone number, email address, birthday, age, race, ethnicity, social security number, marital status, employer information, spouse information, etc. User data [326] can further include salubrity-related information, such as but not limited to: patient type (e.g., outpatient, inpatient, emergency department, urgent care), salubrity care coverage information, salubrity care providers involved in the user's care. etc. In some implementations, user data [326] can include additional patient- and provider-reported salubrity data, such as information associated with diagnoses, medications, family medical history, lab and test results, biometric data, treatment history, etc. One or more types of user data [326] may be collected and used for CHIP qualification determinations based on permissions provided by the user. Other types of user data [326] are possible and are within the scope of the present disclosure.

According to further aspects, the questionnaire generator [350] is configured to perform a pre-qualification determination, wherein one or more CHIP rules [316] and associated service provider policy rules are applied to the collected user data [326]. For example, CHIP rules [316] associated with a CHIP can be used by the questionnaire generator [350] to determine whether the collected user data [326] satisfies qualification criteria for the assistance program. The pre-qualification determination results can include one or more CHIPs that the user qualifies for, one or more CHIPs that the user does not qualify for, and/or one or more CHIPs that the user may qualify for but that additional qualification data are needed for making the qualification determination. For example, the one or more CHIPs that the user qualities for can be added to a list of CHIP candidates for the user. The one or more CHIPs that the user does not qualify for may be removed from consideration and accordingly, additional qualification data may not be requested for those assistance programs.

For a CHIP that the user may qualify for but that additional qualification data are needed for making the qualification determination, the questionnaire generator [350] is configured to determine what qualification data may be missing from the collected user data [326], and to generate or obtain one or more questions directed to the user for ascertaining additional qualification data that correlate with the missing data. For example, each question may be directed to specific additional qualification data that are needed for making a determination whether qualification criteria for a CHIP are satisfied and to enforce the service provider's CHIP policy. Accordingly, the questionnaire generator [350] may generate or access the data. store [365] to select a question [338] that requests the user's input for a response defining the user's need(s), and may include that specific question in a questionnaire directed to the user. Pre-generated questions [338] may be associated with particular CHIP qualification criteria. For example, if a particular CHIP offers financial assistance to users who meet qualification criteria associated with a particular household size, gross annual household income, and assets (e.g., bank or retirement account assets), at least three questions [338] may be pre-generated for that CHIP and stored: a first question directed to requesting a user response defining the user's cerebral salubrity requirements, a second question directed to requesting a user response defining the user's relationship(s), and a third question directed to requesting a user response defining the user's empathy. In some implementations, the questions [338] are configured with particular selectable responses (e.g., a dropdown box/selectable options of cerebral salubrity needs, relationship types, and empathy markers). According to aspects, the questionnaire generator [350] is further configured to include one or more questions [338] associated with needed/missing qualification data in a questionnaire, and to transmit the questionnaire to the self-service platform [340] for display to the user. In some further examples, the questionnaire is stored in the data store [365]. As should be appreciated, the terms "question" and "questions" are used herein to describe a word or phrase that can be displayed to the user so as to elicit specific information from the user. That is, questions [338] are not limited to interrogative expressions.

According to further aspects of the present disclosure, the questionnaire includes a reduced set of questions [338]. That is, by first determining the qualification data needed to make a qualification determination for the user; accessing available data sources (e.g., user data [326]) to determine what of that qualification data is already available; applying the CHIP rules [316] including service provider policy rules to the already-available qualification data for determining which CHIPs the user pre-qualifies for, which CHIPs that the user does not qualify for, and which CHIPs the user may qualify for but that additional qualification data is needed to make the qualification determination, the number of questions [338] is reduced to a minimized number of questions to obtain only the additional qualification data needed to make the qualification determination. This, in addition to other benefits, reduces the amount of data input by the user, decreases or eliminates a transmission of sensitive data (e.g., medical-related data), and can also improve the user experience (e.g., by simplifying the CHIP application process for the user).

In various implementations, the questionnaire generator [350] is configured to receive a request for the questionnaire from the self-service portal [340]. For example, the questionnaire generator [350] can provide a questionnaire API and instructions (e.g., markup language code, scripting language code, functions) for the self-service portal [340] to request the questionnaire from the questionnaire generator [350]. Responsive to the request, the questionnaire generator [350] responds to the request with an API response that includes the questionnaire and instructions for enabling the self-service portal [340] to generate a UI [320] including the questionnaire (e.g., the set of questions [338] for obtaining the additional qualification data needed to make the qualification determination). In example aspects, the API response includes instructions that define the layout of the questionnaire, and may also support different user computing device [202a] form factors (e.g., mobile, table, desktop). In various aspects, the UI [320] displayed to the user includes the questionnaire and input controls (e.g., fillable data fields, checkboxes, dropdown lists, or selectable buttons) enables the user to enter user input in response to the one or more questions [338] included in the questionnaire.

In other examples, the screening engine [360] provides/exposes a screening API, Which the self-service portal [340] can invoke to communicate the user responses (to the questions [338] included in the questionnaire) to the screening engine [360] as part of a request for CHIP qualification results. For example, the screening engine [360] includes one or more APIs, which connect the self-service portal [340] to the screening engine [360] so that the self-service portal is able request CHIP qualification results from the screening engine, to transmit data input by the user via the user computing device [202a] to the screening engine for determining whether the user qualifies for a CHIP, and to receive the determination results in an API response from the screening engine.

In example aspects, the screening engine [360] is illustrative of one or more computing devices, software applications, or modules operative or configured to receive user responses to the questions [338] included in the questionnaire, wherein the user responses include the additional qualification data needed to make one or more CHIP qualification determinations for the user, and to apply one or more CHIP rules [316] and service provider policy rules to the received additional qualification data (i.e., user response data), user data [326] to determine whether the qualification data (i.e., user response data, user data [326]) satisfy qualification criteria for one or more CHIPs.

In various aspects, as part of determining whether the user qualifies for a CHIP, the screening engine is further configured to determine a level or amount of assistance a CHIP may provide. For example, CHIP rules [316] can define specific actions to take when qualification criteria for a CHIP are met. One example of a specific action can include an instruction to approve the user for qualification for the CHIP and to apply a particular percentage discount or a particular dollar amount discount to offered products included in an ongoing transaction record [328] for the user. The discounted obligation amount can be included in a qualification determination result.

In some further example, the screening engine [360] is further configured to rank the qualification determination results based on the discounted obligation amounts. For example, based on an application of CHIP rules [316] and associated service provider policy rules to the user response data, user data [326], the screening engine [360] may determine that the user qualifies for two CHIPs. A first CHIP qualification determination result may indicate that the user qualifies for a 10% discount of the user's obligation amount (e.g., $1000), resulting, in a discounted obligation amount of $900. A second CHIP qualification determination result may indicate that the user qualifies for a 20% discount of the obligation amount, resulting in a discounted obligation amount of $800. The screening engine [360] may rank these two qualification determination results based on the discounted obligation amounts such that the second qualification determination result is ranked higher than the first qualification determination result. Some examples of obligation discounts are financial need, PNP referral, repeat use of provider, and/or multi-CHIP enrollment.

According to one additional aspect of the disclosure, the screening engine [360] is configured to generate a CHIP qualification results response based on the qualification determination result(s) for the user. For example, responsive to the CHIP qualification results request, the screening engine [360] responds to the request with an API response that includes CHIP qualification results and instructions for enabling the self-service portal [340] to generate a UI [320] including an indication of whether the user qualifies for a CHIP and if the user qualifies for a CHIP, input controls that enable the user to select and enroll in the CHIP for which the user is qualified. In additional examples, the API response includes instructions that define the layout of the results feedback and may support different user computing device(s) [202a] form factors (e.g., mobile, table, desktop).

According to an example aspect, the CHIP qualification results response includes a listing of CHIPs that the user qualifies for in association with a particular ongoing transaction record [328]. For example, if the user has multiple ongoing transaction records [328], the user may qualify for one or more CHIPs for one or more of the individual ongoing transaction records. According to another example aspect, the CHIP qualification results response includes a ranked listing of CHIPs for which the user qualifies, including the offers and referrals. In some implementations, if the user qualifies for more than one CHIP for a particular ongoing transaction record [328], the screening engine [360] is configured to include only the highest ranked CHIP in the CHIP qualification results response. For example, if the user qualifies for a first CHIP that offers a substance abuse treatment and also qualifies for a second CHIP that does not offer substance abuse treatment, only the first CHIP may be included in the CHIP qualification results response is the user's need is a substance abuse program. Likewise, CHIPs that do not accept a PNP with a substance abuse need will not be offered or referred to PNPs having such a need.

In some examples, enrollment in one CHIP may conflict with enrollment in another CHIP based on certain CHIP rules [316] and/or associated service provider policies. In such cases, the screening engine [360] is configured to include instructions in the CHIP qualification results response that enable the self-service portal [340] to prevent conflicting enrollment selections. For example, if the user selects to enroll in a first CHIP and that program does not allow for enrollment in another CHIP, the self-service portal [340] can execute the instructions to disable input controls for selecting and enrolling in other (conflicting) CHIPs.

Here, if the user does not qualify for a CHIP, the CHIP qualification results response includes a notification that the user does not qualify for a CHIP. In another example aspect, if the user does not qualify for a CHIP, the CHIP qualification results response includes a link to a settlement plan system configured to provide a settlement plan for the user to settle according to a schedule over a period of time.

The enrollment engine [370] is illustrative of one or more computing devices, software applications, and/or modules operative or configured to receive a request for enrollment in one or more CHIPs from the self-service portal [340]. In additional examples the enrollment engine [370] provides/exposes an enrollment API, which the self-service portal [340] can invoke to communicate an enrollment selection to the enrollment engine [370] as part of a request for automated enrollment in a CHIP. For example, the screening engine [360] includes one or more APIs, which connect the self-service portal [340] to the enrollment engine [170] so that the self-service portal is able send enrollment selections and the enrollment request.

The enrollment engine [370] is configured to receive the request for enrollment in one or more selected CHIPs. According to some aspects, the enrollment engine [370] includes a set of code that evaluates the CHIP rules [316] and the associated service provider policy rules associated with enrollment criteria for the selected CHIPs against data previously collected for the user (user data [326] and user response data) for determining whether supplementary data is needed to enroll the user in the one or more CHIPs. For example, supplementary data can include additional user input data and/or supporting documents.

CHIP rules [316] can define specific actions to take when qualification criteria for a CHIP are met and the user selects to enroll in the CHIP. For example, CHIP rules [316] may define an action to provide information to the user associated with completing the enrollment process. One example of a specific action can include an instruction to request certain additional user input (e.g., user signature, demographic data, financial data, salubrity-related data) or particular supporting documents (e.g., bank statements, tax documents, income documents) from the user. For example, the rule action can include an instruction to include one or more additional questions [338] and/or a document upload interface in an API response to the self-service portal [340].

In example aspects, the enrollment engine [370] is configured to generate an enrollment response based on the result(s) of additional user input determination(s). For example, responsive to the enrollment request, the enrollment engine [370] responds to the request with an API response that includes instructions for enabling the self-service portal [340] to generate a UI [320] including instructions for completing enrollment (e.g., instructions associated with additional user input or particular supporting documents needed from the user to complete the enrollment process for one or more selected CHIPs) and input controls (e.g., fillable data fields, checkboxes, dropdown lists, or selectable buttons) that enable the user to enter additional user input (e.g., user signature, demographic data, salubrity-related data) and/or a document upload interface that enables the user to upload and transmit supporting documents (e.g., medical records, images, provider assigned task deliverables) to the enrollment engine [370].

In some aspects, the enrollment engine [370] is configured to access one or more forms, such as application or enrollment forms corresponding to the one or more selected CHIPs, to pre-fill one or more fields of the one or more forms with previously collected for the user (user data [326], and user response data), and include the form with unfilled fields in the enrollment response. In example aspects, the API response includes instructions that define the layout of the instructions, input controls, and/or document upload interface, and may support different user computing device [202a] form factors (e.g., mobile, table, desktop).

According to another aspect of the disclosure, the enrollment engine [370] is further configured to receive inputs entered into the self-service portal [340] by the user (e.g., user signature, demographic data, salubrity-related data, supporting documents). For example, the enrollment engine [370] provides/exposes an API, which the self-service portal [340] can invoke to communicate, user inputs to the enrollment engine [370] for completing the user's enrollment in one or more CHIPs.

Another example of a specific action defined by CHIP rules [316] can include an instruction to communicate an enrollment request to one or more of the service provider system(s) [304], and a patient access workflow system [390] associated with a service provider system. In various examples, the service provider system [304] may utilize a patient access workflow system [390] to perform one or more patient access workflow processes. The patient access workflow system [390] may be implemented on a computing device (e.g., server computing device, a cloud-based server computing device, desktop computing device) of the service provider system [304] or in communication with the service provider system.

According to an aspect, the enrollment engine [370] is configured to execute the specific action and communicate the users enrollment request to the corresponding service provider system(s) [304], and/or patient access workflows system [390]. In some example aspects, the enrollment engine [370] invokes an API of the service provider system(s) [304] to enroll the user in a CHIP. For example, the API connects the enrollment engine [370] to the service provider system(s) [304], and/or patient access workflow system [390] associated with the provider system(s) so that the enrollment engine [370] is able to transmit an indication of the user's selection to enroll in a CHIP and associated data (e.g., user data [326], user inputs, supporting documents) to the corresponding service provider system(s) [304], and in some examples, a patient access workflow system [390] associated with the provider system(s). Aspects of the ICSRSS [330] enable the user to gather and transmit sensitive supporting documents only when the user knows that he/she qualifies and has selected to enroll in a CHIP. As can be appreciated, this can improve data security, computing resources associated with uploading and transmitting the documents, and the user experience.

According to another embodiment, the enrollment engine [370] is configured to receive an indication of completion of the CHIP application and enrollment process from one or more of the service provider system(s) [304], and patient access workflow system [390]. Responsive to receiving the indication of completion, the enrollment engine [370] may update the data store [365] with a CHIP application and enrollment process status update. For example, the status of the user's CHIP application for and enrollment in a CHIP can be stored by the ICSRSS [330]. In various examples, the ongoing transaction records [328] for the user may be updated with discounted offers and referrals. Accordingly, when the user uses these self-service portal [340] to view his/her services, the self-service portal obtains the updated offers for display to the user. In some examples, the enrollment engine [370] may be configured to communicate the completion of the CHIP application to the user via the self-service portal [340] or via one or more other communication means (e.g., text message, email, phone call, mail).

Figure 4:
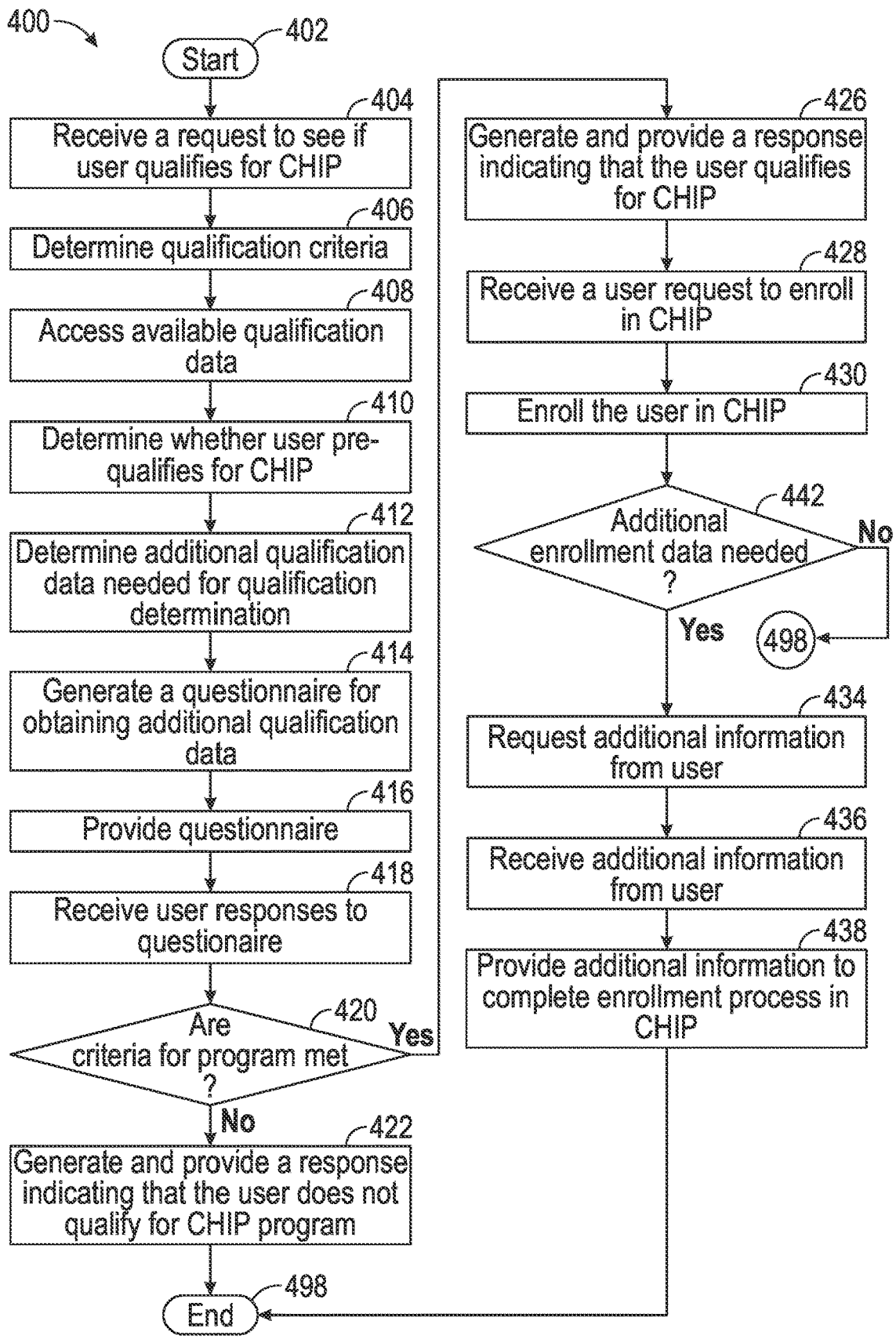
FIG. 4 is a flow chart showing general stages involved in an example system that provides an immersive cerebral salubrity retention and selection package (ICSRSP) according to an embodiment.

FIG. 4 is a flow chart showing general stages involved in an example system [400] for providing an ICSRSP according to one embodiment. An example system [400] for providing an ICSRSP begins at START OPERATION [402] and proceeds to OPERATION [404], where the example system [400] uses the questionnaire generator [350] of the ICSRSS [330] to receive a request from the self-service portal [340] to determine whether the user qualifies for a CHIP. In various examples, the qualification request is received responsive to the user logging into the self-service portal [340], the self-service portal providing an indication of CHIP(s) associated with one or more ongoing transaction records [328] related to services received from one or more service providers in a UI [320] for display to the user, and a user-selection to determine whether the user meets criteria for one or more CHIPs. In another example, the qualification request is automatically generated when an ongoing transaction record [328] for the user is received from a service provider system [304] by the ICSRSS [330]. In a further example, the service provider system [304] may send a batch of new ongoing transaction records [328] to the ICSRSS [330] on a scheduled basis (e.g., daily, nightly, weekly). In another example aspect, the service provider system [304] may send a new ongoing transaction record [328] to the ICSRSS [330] when the new record is created. According to this embodiment, the qualification request includes information identifying the user and the service provider associated with the ongoing transaction record [328].

At OPERATION [406], the example system [400] uses the questionnaire generator [350] to determine qualification data associated with qualification criteria for one or more CHIPs offered by one or more CHIP providers who are part of the salubrity care service provider, one or more CHIP providers who have contracted with the salubrity care service provider, or one or more third-party CHIP providers. In example aspects, the questionnaire generator [350] accesses CHIP rules [316] for available CHIPs and service provider policy rules for the service providers associated with the user's ongoing transaction records [328] for determining qualification criteria for the CHIPs. For example, the qualification criteria can be defined in conditions (e.g., if statements) of the CHIP rules [316] and associated service provider policy rules.

At OPERATION [408], the example system [400] uses the questionnaire generator [350] to access available qualification data associated with the qualification criteria. For example, the user data [326] can be provided by one or more service provider systems [304] prior to the qualification request and stored in the data store [365] or can be provided by a service provider system responsive to a request for the user data.

At OPERATION [410], the example system [400] uses the questionnaire generator [350] to apply the CHIP rules [316] and associated service provider policy rules to the user's user data [326] for one or more of: one or more CHIPs that the user qualifies for, one or more CHIPs that the user does not qualify for, and/or one or more CHIPs that the user may qualify for but that additional qualification data are needed for making the qualification determination.

For a CHIP that the user may qualify for but that additional qualification data are needed for making the qualification determination, at OPERATION [412], the example system [400] uses the questionnaire generator [350] to determining what qualification data may be missing from the collected user data [326] based on the CHIP rules [316] and associated service provider policy rules. For example, the additional qualification data needed to make the qualification determination(s) may include certain information that may not be included in the collected user data [326], information that may need to be updated or verified by the user, or inconsistent data (e.g., different names for the user in user data [326]).

At OPERATION [414], the example system [400] uses the questionnaire generator [350] to generate a questionnaire including one or more questions [338] directed to the user based on the additional qualification data needed for making the qualification determination. The one or more questions [338] can be pre-generated questions or can be generated dynamically.

At OPERATION [416], the example system [400] uses the questionnaire generator [350] to provide the questionnaire to the self-service portal [340] for display to the user. In various examples, the questionnaire is provided to the self-service portal [340] in an API response to a request for the questionnaire or the qualification request.

In response to the self-service portal [340] generating and displaying a UI [320] including the questionnaire, receiving user input/responses to the questions [338] via the UI, and sending those user input/responses to the screening engine [360] (e.g., as part of a qualification results API request), at OPERATION [418], the example system [400] uses the screening engine [360] to receive the additional qualification data included in the user input/responses.

At DECISION OPERATION [420], the example system [400] uses the screening engine [360] to make one or more qualification determinations. For example, at DECISION OPERATION [420], the screening engine [360] applies one or more CHIP rules [316] and service provider policy rules to the received additional qualification data (i.e., user response data) and user data [326] to determine whether the qualification data (i.e., user response data and user data [326]) satisfy qualification criteria for one or more CHIPs.

When a determination is made that the qualification data do no satisfy qualification criteria for a CHIP, at OPERATION [422], the example system [400] uses the screening engine [360] to generate and communicate a response to the self-service portal [340] that indicates that the user does not qualify for a CHIP. In various examples, in the response, the screening engine [360] may include a link to a self-help system, which the user can navigate to request a self-help plan for cerebral salubrity according to a schedule over a period of time.

When a determination is made (at DECISION OPERATION [420]) that, the qualification data satisfies qualification criteria for a CHIP, at OPERATION [424], the example system [400] uses the screening engine [360] to offers and referrals corresponding to each CHIP for which the user qualifies. The example system [400] may further use the screening engine [360] to rank the CHIPs according to the needs of the PNP.

At OPERATION [426], the example system [400] uses the screening engine [360] to generate and communicate a response to the self-service portal [340] based on the results of the qualification determination. For example, the response can include information that indicates that the user qualifies for one or more CHIPs and the associated offers and referrals.

In response to the self-service portal [340] generating and displaying a UI [320] including an indication of the qualification determination(s), receiving a user selection to apply for/enroll in one or more of the CHIPs for which the user qualifies, and communicating those selections to the enrollment engine [370] (e.g., as part of an enrollment API request), at OPERATION [428], the example system [400] uses the enrollment engine [370] to receive the user's selection(s) as a request to apply for/enroll in the selected assistance program(s), At OPERATION [430], the example system [400] uses the enrollment engine [370] to enroll the user in the selected CHIP(s) by communicating the user's enrollment selection(s) as part of an enrollment request (e.g., an API call or other communication medium) directed to one or more of the corresponding service provider system(s) [304], and/or the corresponding service provider system(s) via the patient access workflow system [390].

At DECISION OPERATION [432], the example system [400] uses the enrollment engine [370] to determine whether additional user input (e.g., user signature, demographic data, salubrity-related data) and/or particular supporting documents (e.g., medical records, provider assigned deliverables, images) may be needed to complete the enrollment process for a CHIP (e.g., according to CHIP rules [316] and/or associated service provider policies).

When a determination is made that additional user input and/or supporting documents are needed to complete the enrollment process for the user, the example system [400] uses the enrollment engine [370] at OPERATION [434] to generate or select one or more supplementary questions [338] directed to the user based on the additional user-provided data needed for enrolling the user in one or more CHIPs, and to respond to the user's enrollment request with a response communicated to the self-service portal [340] including the one or more supplementary questions [338] associated with the needed user input data, a list of supporting documents (e.g., documents that serve as a proof of address, proof of income, proof of employment, proof of assets, proof of student status, proof of a medical condition or disability, proof of military service) required by the CHIP(s) and/or service provider(s), and an interface for uploading the supporting documents.

In response to the self-service portal [340] generating and displaying a UI [320] including the supplementary questions [338], the list of required supporting documents, and the interface for uploading the supporting documents receiving user input/responses to the supplementary questions [338] and/or one or more supporting documents, and sending those user input/responses and/or supporting documents to the enrollment engine [370], the example system [400] uses the screening engine [360] at OPERATION [438] to receive the user input/responses and/or supporting documents and to provide those user input/responses and/or supporting documents to one or a combination of: the corresponding service provider system(s) [304] and the corresponding service provider system(s) via the patient access workflow system [390]. In example aspects, the service provider system(s) [304] may update the user's ongoing transaction records [328] with offers and referrals, and these updated ongoing transaction records can be transmitted to the ICSRSS [330] and stored in the data store [365]. The example system [400] ends at OPERATION [498].

In another aspect of this disclosure, the determination of whether the user qualifies for a CHIP is made in near real-time after user submits inputs for the questionnaire. Therefore, the user does not have to wait for a long time to know whether he/she qualities for a CHIP. In addition, the screening questionnaire does not require the user to provide any documents. Therefore, the user can respond to the questionnaire in a shortened amount of time. Further, aspects of the disclosure obviate a need to collect and transmit sensitive information and sensitive supporting documents knowing the user's eligibility for a CHIP. This results in a reduction of an amount of information to be submitted, thereby reducing the complexity of applying for and enrolling in a CHIP. In addition, aspects of the disclosure accelerate the process for determining whether user qualifies for a CHIP by eliminating one or more manual review processes. For example, a reduced amount of information is provided to an administrator of the service provider system [304], and the administrator may only be required to review information submitted by users who have been determined to qualify for the CHIP(s). In addition, by first determining the user's qualification for a CHIP and collecting only the data relevant to CHIPs that the user qualifies for, the example system [400] can reduce the amount of time to enroll in and receive the benefits of the CHIP.

An operating system for example, may be suitable for controlling the operation of computing devices. Furthermore, aspects of this disclosure may be practiced in conjunction with a graphics library, other operating systems, or any other application program and is not limited to any particular application or system. Computing devices may also include one or more input device(s) (keyboard, mouse, pen, touch input device, etc.) and one or more output device(s) (e.g., display, speakers, a printer, etc.).

Computing devices may also include additional data storage devices (removable or non-removable) such as, for example, magnetic disks, optical disks, or tape. Such additional storage is illustrated by either removable storage and non-removable storage. Computing devices may also contain a communication connection that may allow computing devices to communicate with other computing devices, such as over a network in a distributed computing environment, for example, an intranet or the Internet. Communication connection is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit including discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present invention may be used in various distributed computing environments where tasks are perforated by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing devices or any other computing devices, in combination with computing device, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

I claim:

1. One or more user computing devices comprising computing a provision of an automated response to one or more individuals said devices comprising:
at least one data processor device; and
a memory storage device operatively connected to said at least one data processor device with instructions that is executed by said at least one processor device and is configured to provide a request generator, said request generator generates a request and is configured to receive a request from one or more individuals that become receivers and determine if one or more potential new patients (PNPs) will receive an immersive cerebral salubrity retention and selection package (ICSRSP) that manages customized cerebral care together with available advising session time periods to begin improvement of said individuals' cerebral care, wherein said ICSRSP [that] includes said one or more receivers that receive a list of networked customized cerebral salubrity care personnel by receiving a plurality of program provider rules, each respective program provider rule comprising one or more sets of respective program provider rules, wherein at least one rule of at least one of a plurality of a set of program provider rules indicates a clinical condition and a possible clinical conclusion;

wherein said user computing device is at least one of many types of computing devices including but not limited to mobile devices, laptop computers, desktop computers, wearable computing devices, and other computing devices suitable to access a self-service portal system, which provides a user interface through which a user via one or more processors can view ongoing transactions, view and provide answers to a set of qualification questions for determining eligibility of a user for a cerebral health immersion program known as a CHIP, receive a CHIP qualification/eligibility response, and upload and transmit supporting documentation and provide a digital signature to a data processor system configured to communicate with a data processor system via a computerized network that is a public or private data network for communicating data between computer systems with different entities and at different geographic locations that creates an ability for one or more receivers to complete one or more interrogatives that determine if said one or more receivers are disqualified as a client based on responses that include past and current cerebral salubrity needs and future expectations that said one or more receivers describe with regard to their specific individual cerebral salubrity care issues and wherein program provider rules are applied to consider data acquired from said one or more receivers that are in receipt of said ICSRSP such that said devices retrieve PNPs data that includes one or more PNPs personal information on selected from a group consisting of: past and current state of cerebral salubrity, human interactions, relationships, and wealth status conditions to analyze cerebral salubrity care service needs, and wherein:

a computational host acts on behalf of one or more salubrity care service personnel to predetermine if a PNP can be provided said ICSRSP as determined by one or more cerebral salubrity care service personnel by collection of personal information data via receipt of said personal information data from said PNPs, wherein said personal information on data includes retrieval of wealth status data that can also include retrieval from a third-party wealth status data source, and wherein said personal information is data that further includes data generated from and response to a request comprising at least three interrogatives, wherein said interrogatives correlate with personal information data that does not include personal PNP wealth status data; and wherein said devices transmit said request to a portal configured to generate a potential new patient (PNP) graphical user interface for display to one or more PNPs, wherein said PNP graphical user interface includes said request;

and wherein said one or more salubrity care personnel receive PNP responses to said request via said PNP graphical user interface; and transmits said responses to a filter determinator that is configured to;

receive PNP responses;

assess said PNP responses, personal PNP data, and PNP wealth status data by utilization of said filter determinator to assist with final determination of said responses that includes specific criteria and determines via a final determinator if reception of an ICSRSP is justified via said specific criteria and;

transmits a response to a portal for display to said PNP in said PNP graphical user interface and;

also provides an acceptance determinator, said acceptance determinator configured to receive, via a portal, a request for acceptance into said ICSRSP in order for said PNP to become a bona fide client by identification via said filter determinator if said PNP is allowed based upon program rules that provides acceptance of said PNPs concurrent with all program rules and data provided by said client and said computational host, wherein said specific criteria is embedded within said filter determinator and includes at least three interrogatives comprising:

(i) said PNPs immediate cerebral salubrity issue, (ii) timing and length of time required to address said PNPs cerebral salubrity needs, and;

(iii) PNPs ability to engage to succeed by an improvement in cerebral salubrity with customized cerebral salubrity care providers that possess associated advising time periods determined by one or more members of said host and further determines if said PNP is allowed to receive ICSRSP assistance and become a bona fide client.

2. The devices of claim 1, wherein if said specific criteria and said host individually and/or separately determine if a PNP becomes said bona fide client said bona fide client is informed of a decision by transmission of data that is in a form of a response to said portal for display to said PNP via said PNP user interface, wherein said PNP user interface is displayed on one or more of a group of selected virtual or real devices consisting of: a smart and/or cellular mobile phone, a laptop computer, a desktop computer, a smart watch, a television and a theatre screen.

3. The devices of claim 1, wherein if said PNP is deemed allowable, said PNP is directed to an auto link that provides R-Rx products to said PNP, wherein said R-Rx products are a collection of treatment options to assist an accepted client with relationship issues that include both low cost and free resources available from at least one of a group consisting of: e-books, videos, in-person and on-line advising, seminars, webinars, and hard copy books and manuals.

4. The devices of claim 3, wherein if said clients do not acquire one or more treatment packages that are a portion of said ICSRSP, said clients receive a series of electronic communications and subsequent notifications that continue to be sent until said accepted clients acquire said treatment packages or said accepted clients notify said host to cease and desist from future electronic communications.

5. The devices of claim 1, wherein if said PNP is deemed at least partially allowed into said ICSRSP a potential client is directed to a video that plays in a range of 45 to 90 minutes and/or an in-person session with a trained associate to ascertain if said at least three interrogatives have been completed.

6. The devices of claim 5, wherein if said receivers do not pass all assessments, said receivers receive information that provides said receivers with one or more other hosts and a series of electronic communications that provide R-Rx products.

7. The devices of claim 5, wherein a determination of said accepted client's information utilizes a request generator configured to send and also receive a request for a determination of one or more PNPs data and continue receipt of records to evaluate ongoing improvement in said accepted clients' cerebral salubrity.

8. The devices of claim 5, wherein said ICSRSP is securitized with one or more devices comprising a real or virtual master distributed auto-synchronous array (DASA) database (dB) located within or external to said devices that at least stores and retrieves data and that includes at least two or more partial distributed auto-synchronous array (DASA) dBs wherein said partial DASA dBs function in either an independent manner, a collaborative manner or both, and wherein said master and partial DASA dBs allow for bi-directional transmission of data to and from multiple partial user devices, to and from multiple partial access devices or to and from both partial user and partial access devices, wherein said one or more partial user and access devices store and provide at least partial copies of portions of said master DASA dB and wherein said master DASA dB, said partial DASA dBs or both partial and master DASA dBs are linked and communicate with each other as well as one or more logging and monitoring dBs capable of statistical and numerical calculations utilizing said data, wherein said tools authenticate using a first set of computing operations, validates using a second set of computing operations, and wherein a third set of computing operations controls access for a specified set of users.

9. The devices of claim 5, wherein said devices utilize an artificial intelligence and machine learning infrastructure system comprising:
one or more storage systems comprising, respectively, one or more storage devices included within respective storage arrays controlled by respective one or more storage controllers; and
one or more graphical processing units, wherein the graphical processing units are configured to communicate with the one or more storage systems over a communication fabric;
wherein said one or more storage systems, said one or more graphical processing units, and said communication fabric is implemented within a single chassis; and
wherein said one or more storage systems are configured to:
receive, at a storage system from said one or more graphical processing units via a storage system application program interface (API) provided by said storage system directly to said one or more graphical processing units and configured to provide specification of one or more data storage operations, one or more data storage operations specifying storage of multiple data objects that respectively include data and metadata describing one or more attributes of said data;
receive, at said storage system from said one or more graphical processing units via said storage system API further configured to provide specification of one or more queries that operate on metadata for said multiple data objects, a query that includes metadata that specifies one or more attributes of data;
generate, based on said storage system searching through said metadata of data objects stored in said storage system, a dataset that includes one or more of said multiple data objects such that said metadata of each data object in said dataset satisfies said one or more attributes of data specified by said the metadata included in said query; and
transmit, from said storage system to said one or more graphical processing units over said communication fabric, said dataset of said one or more of said multiple data objects.

10. The devices of claim 1, wherein if said PNP becomes a client by passing all assessments, said client is then encouraged to engage with said host and receive an ICSRSP package with an allocation for at least 6 months and to receive an unlimited treatment and access to ICSRSP management personnel with advising times available throughout a 24/7 time period during said unlimited treatment.

11. The devices of claim 10, wherein said unlimited treatment further comprises provision of salubrity products, access to private locked waiting virtual and/or real waiting areas, and electronic communication options including personal notes taken during salubrity sessions.

12. The devices of claim 10, wherein said unlimited treatment further comprises automated acceptance with on-line links for additional time period access with said host and a series of electronic communications that include text, video, and voice about salubrity products.

13. One or more user computer systems that provides computing a provision of an automated response to one or more individuals that are initially receivers and receive an immersive cerebral salubrity management program comprising customized cerebral salubrity care with advising time periods to begin improvement of said individuals' cerebral salubrity, said systems comprising:
to one or more individuals that receive an immersive cerebral salubrity retention and selection package (ICSRSP) that manages customized cerebral care together with available advising session time periods to begin improvement of said individuals' cerebral care, said devices comprising:
at least one processor device; and
a memory storage device operatively connected to said at least one data processor device with instructions that is executed by said at least one processor device and is configured to provide a request generator, said request generator generates a request and is configured to receive a request from one or more individuals that become receivers and determine if one or more potential new patients (PNPs) will receive an immersive cerebral salubrity retention and selection package (ICSRSP) that manages customized cerebral care together with available advising session time periods to begin improvement of said individuals' cerebral care, wherein said ICSRSP includes said one or more receivers that receive a list of networked customized cerebral salubrity care personnel receiving a plurality of program provider rules, each respective program provider rule comprising one or more sets of respective program provider rules, wherein at least one rule of at least one of a plurality of a set of program provider rules indicates a clinical condition and a possible clinical conclusion;
wherein said user computing systems are at least one of many types of computing systems with computing devices that are networked including but not limited to mobile devices, laptop computers, desktop computers, wearable computing devices, and other computing devices suitable to access a self-service portal system, which provides a user interface through which a user via one or more processors can view ongoing transactions, view and provide answers to a set of qualification questions for determining eligibility of a user for a CHIP, receive a CHIP qualification/eligibility response, and upload and transmit supporting documentation and provide a digital signature to a networked data processor system configured to communicate with a data processor system via a computerized network that is a public or private data network for communicating data between computer systems with different entities and at different geographic locations that creates an ability for one or more receivers to complete one or more interrogatives that determine if said one or more receivers are disqualified as a client based on responses that include past and current cerebral salubrity needs and future expectations that said one or more receivers describe with regard to their specific individual cerebral salubrity care issues and wherein program provider rules are applied to consider data acquired from said one or more receivers that are in receipt of said ICSRSP such that said devices retrieve PNPs data that includes one or more PNPs personal information selected from a group consisting of: past and current state of cerebral salubrity, human interactions, relationships, and wealth status conditions to analyze cerebral salubrity care service needs, and wherein:

a computational host acts on behalf of one or more salubrity care service personnel to predetermine if a PNP can be provided said ICSRSP as determined by one or more cerebral salubrity care service personnel by collection of personal information data via receipt of said personal information data from said PNPs, wherein said personal information data includes retrieval of wealth status data that can also include retrieval from a third-party wealth states data source, and wherein said personal information is data that further includes data generated from and response to a request comprising at least three interrogatives, wherein said interrogatives correlate with personal information data that does not include personal PNP wealth status data;

and wherein said devices transmit said request to a portal configured to generate a potential new patient (PNP) graphical user interface for display to one or more PNPs, wherein said PNP graphical user interface includes said request;

and wherein said one or more salubrity care personnel receive PNP responses to said request via said PNP graphical user interface; and transmits said responses to a filter determinator that is configured to;

receive PNP responses;

assess said PNP responses, personal PNP data, and PNP wealth status data by utilization of said filter determinator to assist with final determination of said responses that includes specific criteria and determines via a final determinator if reception of an ICSRSP is justified via said specific criteria and;

transmits a response to a portal for display to said PNP in said PNP graphical user interface and;

also provides an acceptance determinator, said acceptance determinator configured to receive, via a portal, a request for acceptance into said ICSRSP in order for said PNP to become a bona fide client by identification via said filter determinator if said PNP is allowed based upon program rules that provides acceptance of said PNPs concurrent with all program rules and data provided by said client and said computational host, wherein said specific criteria is embedded within said filter determinator and includes at least three interrogatives comprising:

(i) said PNPs immediate cerebral salubrity issue, (ii) time period and timing required to address said PNPs cerebral salubrity needs, and (iii) PNPs ability to engage effectively with customized cerebral salubrity care personnel with associated advising time periods that is determined by one or more members of said host and further determines if said PNP can receive assistance and become a bona fide client.

14. The system of claim 13, wherein said specific criteria and said host that individually and/or separately determines if a PNP is accepted to become a client is informed of a decision by transmission of data that is in a form of a response to said portal for display to said PNP via said PNP graphical user interface that displays said response on one or more of a group of selected devices consisting of: a smart and/or cellular mobile phone, a laptop computer, a desktop computer, a smart watch, a television and a theatre screen.

15. The system of claim 14, wherein if said PNP is deemed disqualified said PNP is directed to an auto link that provides R-Rx products to said PNP, wherein said R-Rx products are a collection of treatment options to assist an accepted client with relationship issues that include both low cost and free resources available from at least one of a group consisting of: e-books, videos, in-person and on-line advising, seminars, webinars, and hard copy books and manuals.

16. The system of claim 13, wherein if said PNP is deemed at least conditionally accepted said client is directed to a video that plays in a range of 45 to 90 minutes and/or to an in-person session with a trained associate of said host to clarify said at least three interrogatives have been completed.

17. The system of claim 13, wherein if said PNP becomes a client by passing all assessments , said client is then encouraged to engage with said host and receive an immersive cerebral salubrity management system that manages an ICSRSP with an allocation for at least 6 months and to receive an unlimited treatment and access to a host that provides advising time throughout a 24/7 hour time period during said unlimited treatment.

18. The system of claim 17, wherein said unlimited treatment further comprises salubrity products, access to private locked waiting virtual and/or real waiting areas, and electronic communication options including e-mailing of personal notes taken during salubrity sessions.

19. The system of claim 17, wherein said unlimited treatment further comprises automated acceptance with on-line links for additional time periods and electronic communication series for additional salubrity products.

20. The system of claim 17, wherein if said accepted clients do not acquire said treatment package, they receive a series of electronic communications and subsequent notifications that continue to be sent until they acquire said treatment packages or said accepted clients notify said host to cease and desist from future electronic communications.

21. The system of claim 17, wherein if said receivers do not pass all assessments, they receive information that provides said receivers with one or more other hosts and a series of electronic communications that provide R-Rx products.

22. The system of claim 17, wherein a determination of said clients information utilizes a request generator configured to send and also receive a request for a determination of one or more PNPs data and continue receipt of records to evaluate ongoing improvement in said clients' cerebral salubrity.

23. The system of claim 17, wherein said system is securitized with one or more devices comprising a real or virtual master distributed auto-synchronous array (DASA) dB located within or external to said devices that at least stores and retrieves data and that includes at least two or more partial distributed auto-synchronous array (DASA) dBs wherein said partial DASA dBs function in either an independent manner, a collaborative manner or both, and wherein said master and partial DASA dBs allow for bi-directional transmission of data to and from multiple partial user devices, to and from multiple partial access devices or to and from both partial user and partial access devices, wherein said one or more partial user and access devices store and provide at least partial copies of portions of said master DASA dB and wherein said master DASA dB, said partial DASA dBs or both partial and master DASA dBs are linked and communicate with each other as well as one or more logging and monitoring dBs capable of statistical and numerical calculations utilizing said data, wherein said tools authenticate using a first set of computing operations, validates using a second set of computing operations, and wherein a third set of computing operations controls access for a specified set of users.

24. The system of claim 17, wherein said system utilizes an artificial intelligence and machine learning infrastructure system comprising:
one or more storage systems comprising, respectively, one or more storage devices included within respective storage arrays controlled by a respective one or more storage controllers; and
one or more graphical processing units, wherein the graphical processing units are configured to communicate with the one or more storage systems over a communication fabric;
wherein the one or more storage systems, the one or more graphical processing units, and the communication fabric are implemented within a single chassis; and
wherein the one or more storage systems are configured to:
receive, at a storage system from the one or more graphical processing units via a storage system application program interface (API) provided by the storage system directly to the one or more graphical processing units and configured to provide specification of one or more data storage operations, one or more data storage operations specifying storage of multiple data objects that respectively include data and metadata describing one or more attributes of the data;
receive, at the storage system from the one or more graphical processing units via the storage system API further configured to provide specification of one or more queries that operate on metadata for the multiple data objects, a query that includes metadata that specifies one or more attributes of data;
generate, based on the storage system searching through the metadata of data objects stored in the storage system, a dataset that includes one or more of the multiple data objects such that the metadata of each data object in the dataset satisfies the one or more attributes of data specified by the metadata included in the query; and
transmit, from the storage system to the one or more graphical processing units over the communication fabric, the dataset of the one or more of the multiple data objects.

\* \* \* \* \*